(12) United States Patent
Miyake et al.

(10) Patent No.: US 7,435,842 B2
(45) Date of Patent: Oct. 14, 2008

(54) PROCESS FOR PRODUCING CARBONIC ESTER

(75) Inventors: Nobuhisa Miyake, Kurashiki (JP); Hajime Nagahara, Kawasaki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 598 days.

(21) Appl. No.: 10/495,451

(22) PCT Filed: Dec. 27, 2002

(86) PCT No.: PCT/JP02/13809

§ 371 (c)(1), (2), (4) Date: May 13, 2004

(87) PCT Pub. No.: WO03/055840

PCT Pub. Date: Jul. 10, 2003

(65) Prior Publication Data

US 2005/0080274 A1    Apr. 14, 2005

(30) Foreign Application Priority Data

| Dec. 27, 2001 | (JP) | ............................. 2001-396537 |
| Dec. 27, 2001 | (JP) | ............................. 2001-396545 |
| Mar. 19, 2002 | (JP) | ............................. 2002-076417 |
| Aug. 8, 2002 | (JP) | ............................. 2002-230991 |
| Aug. 9, 2002 | (JP) | ............................. 2002-232544 |

(51) Int. Cl.
    *C07C 69/96*      (2006.01)
(52) U.S. Cl. ....................... 558/260; 558/270
(58) Field of Classification Search ................. 558/270, 558/277, 260
See application file for complete search history.

(56) References Cited

FOREIGN PATENT DOCUMENTS

| JP | 54-3012 A | 1/1979 |
| JP | 58-134053 A | 8/1983 |
| JP | 6-262085 A | 9/1994 |
| JP | 7-33715 A | 2/1995 |
| JP | 2001-247519 A | 9/2001 |
| NL | 6612421 | 3/1967 |

OTHER PUBLICATIONS

Yamazaki et al. (Industrial & Engineering Chemistry Product Research and Development, 1979, 18(4), 249-252.*
Kizlink ( Collect. Czech. Chem. Commun. 1993, 58, 1399-1402.*
T. Sakakura et al., Polyhedron 19:573-576 (2000).
Yamazaki et al., Ind. Eng. Chem. Prod. Res. Dev., vol. 18, No. 4, pp. 249-252 (1979).
Kizlink et al., Collect. Czech. Chem. Commun., vol. 58, pp. 1399-1402 (1993).
Sakai et al., J. Org. Chem., vol. 36, No. 9, pp. 1176-1180 (1971).
Davies et al., J. of Organometallic Chemistry, vol. 256, pp. 251-260 (1983).
English language abstract of JP 54 063023 A (May 21, 1979).

\* cited by examiner

*Primary Examiner*—D. Margaret Seaman
*Assistant Examiner*—Nizal S Chandrakumar
(74) *Attorney, Agent, or Firm*—Birch, Stewart, Kolasch & Birch, LLP

(57) ABSTRACT

A method for producing a carbonic ester, comprising (1) performing a reaction between an organometal compound having a metal-oxygen-carbon linkage and carbon dioxide to obtain a reaction mixture containing a carbonic ester formed by the reaction, (2) separating the carbonic ester from the reaction mixture to obtain a residual liquid, and (3) reacting the residual liquid with an alcohol to form an organometal compound having a metal-oxygen-carbon linkage and form water and removing the water from the organometal compound, wherein the organometal compound obtained in step (3) is recovered for recycle thereof to step (1).

18 Claims, 3 Drawing Sheets

PROCESS FOR PRODUCING CARBONIC ESTER

BACKGROUND OF THE INVENTION

1. Field of the Invention

The present invention relates to a method for producing a carbonic ester from an organometal compound and carbon dioxide. More particularly, the present invention is concerned with a method for producing a carbonic ester, comprising (1) performing a reaction between an organometal compound having a metal-oxygen-carbon linkage and carbon dioxide to obtain a reaction mixture containing a carbonic ester formed by the reaction, (2) separating the carbonic ester from the reaction mixture to obtain a residual liquid, and (3) reacting the residual liquid with an alcohol to form an organometal compound having a metal-oxygen-carbon linkage and form water and removing the water from the organometal compound, wherein the organometal compound obtained in step (3) is recovered for recycle thereof to step (1). By the method of the present invention, a carbonic ester can be produced in high yield from an organometal compound having a metal-oxygen-carbon linkage and carbon dioxide. It is advantageous that carbon dioxide has no toxicity and no corrosiveness and is inexpensive. Further, the method of the present invention is advantageous not only in that the organometal compound after use in this method can be regenerated and recycled to step (1) of the method, thereby preventing occurrence of wastes derived from the organometal compound, but also in that there is no need for the use of a large amount of a dehydrating agent, thereby preventing occurrence of wastes derived from the dehydrating agent. Therefore, the method of the present invention is commercially very useful and has high commercial value.

2. Prior Art

A carbonic ester is a useful compound. For example, a carbonic ester is used as additives for various purposes, such as a gasoline additive for improving the octane number of a gasoline, and a diesel fuel additive for reducing the amount of particles in an exhaust gas generated by the burning of a diesel fuel. A carbonic ester is also used as an alkylation agent, a carbonylation agent, a solvent and the like in the field of the synthesis of organic compounds, such as polycarbonate, urethane, pharmaceuticals and agrichemicals. A carbonic ester is also used as an electrolyte for a lithium battery, a raw material for producing a lubricant oil and a raw material for producing a deoxidizer which can be used for preventing boiler pipes from rusting.

As a conventional method for producing a carbonic ester, there can be mentioned a method in which phosgene as a carbonyl source is reacted with an alcohol, thereby producing a carbonic ester. Since phosgene used in this method is extremely harmful and highly corrosive, this method is disadvantageous in that the transportation and storage of phosgene need minute care and, also, a large cost is needed for the maintenance of production equipment and for assuring safety. Further, this method poses a problem in that it is necessary to dispose of hydrochloric acid, which is by-produced, as a waste.

As another conventional method for producing a carbonic ester, there is known an oxidative carbonylation method in which carbon monoxide as a carbonyl source is reacted with an alcohol and oxygen in the presence of a catalyst, such as copper chloride, thereby producing a carbonic ester. In this method, carbon monoxide (which is extremely harmful) is used under high pressure; therefore, this method is disadvantageous in that a large cost is needed for the maintenance of production equipment and for assuring safety. In addition, this method poses a problem in that a side reaction occurs, such as oxidation of carbon monoxide to form carbon dioxide. For these reasons, it has been desired to develop a safer method for producing a carbonic ester.

In these conventional methods in which phosgene or carbon monoxide is used as a raw material, a halogen, such as chlorine, is contained in the raw material itself or in the catalyst used. Therefore, in the case of these methods, a carbonic ester obtained contains a trace amount of a halogen which cannot be completely removed by a purification step. When such carbonic ester is used as a gasoline additive, a light oil additive or a material for producing electronic equipment, it is possible that the halogen contained in the carbonic ester causes corrosion of equipment. For reducing the amount of a halogen in the carbonic ester to an extremely trace amount, it is necessary to perform a thorough purification of the carbonic ester. For this reason, it has been desired to develop a method for producing a carbonic ester, which does not use any of a halogen-containing raw material and a halogen-containing catalyst.

On the other hand, a method has been put to practical use, in which carbon dioxide is reacted with ethylene oxide or the like to obtain a cyclic carbonic ester, and the obtained cyclic carbonic ester is reacted with methanol, thereby producing dimethyl carbonate. This method is advantageous in that carbon dioxide as a raw material is harmless, and a corrosive substance, such as hydrochloric acid, is substantially not used or generated. However, this method poses the following problems. Ethylene glycol is by-produced in this method; therefore, from the viewpoint of cost reduction, it is necessary to find ways to effectively utilize the by-produced ethylene glycol. Further, it is difficult to perform safe transportation of ethylene (which is a raw material for producing ethylene oxide) and ethylene oxide. Therefore, for removing the need for the transportation, it is necessary that a plant for producing a carbonic ester by this method be built at a location which is adjacent to a plant for producing ethylene and ethylene oxide.

There is also known a method in which carbon dioxide as a carbonyl source is subjected to an equilibrium reaction with an alcohol in the presence of a catalyst comprising an organometal compound having a metal-oxygen-carbon linkage, thereby forming a carbonic ester and water. This equilibrium reaction is represented by the following formula (3):

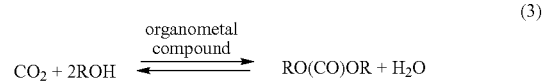

(3)

(R Represents an Unsaturated or Saturated Hydrocarbon Group)

This method is advantageous in that carbon dioxide and an alcohol as raw materials are harmless. However, this method employs an equilibrium reaction in which a carbonic ester and water are simultaneously formed as products. Also in the case of the above-mentioned oxidative carbonylation method using carbon monoxide, water is formed. However, the formation of water in the equilibrium reaction is totally different in significance from the formation of water in the oxidative carbonylation, which is not an equilibrium reaction. The equilibrium of an equilibrium reaction using carbon dioxide as a raw material is thermodynamically biased toward the original system. Therefore, the method using an equilibrium reaction has a problem in that, for producing a carbonic ester in high yield, it is necessary that a carbonic ester and water as products be removed from the reaction system. Further, there is also a problem in that the water formed decomposes a catalyst, so that not only is the reaction hindered, but also the number of turnovers of a catalyst (i.e., number of turnovers of a catalyst (i.e., the number of cycles of regeneration and reuse) is only 2 or 3. For solving this problem, various methods for removing water (which is a product) by using a dehydrating agent have been proposed.

For example, there has been proposed a method in which an alcohol and carbon dioxide are reacted with each other in the presence of a metal alkoxide as a catalyst, thereby forming a carbonic ester and water, wherein a large amount of dicyclohexylcarbodiimide (DCC) (which is an expensive organic dehydrating agent) or the like is used as a dehydrating agent (see Collect. Czech. Chem. Commun. Vol. 60, 687-692 (1995)). This method has a problem in that the dehydrating agent after use cannot be regenerated, resulting in the occurrence of a large amount of a waste derived from the dehydrating agent.

There is known a method for producing a carbonic ester, in which a carboxylic acid orthoester is used as an organic dehydrating agent (see Unexamined Japanese Patent Application Laid-Open Specification No. Hei 11-35521). (In this patent document, there are descriptions reading: "a carboxylic acid orthoester is reacted with carbon dioxide" and "an acetal is reacted with carbon dioxide". However, as a result of recent studies in the art, it is generally presumed that the actual reaction route is as follows. "An alcohol and carbon dioxide are reacted with each other to obtain a carbonic ester and water. A part of the water is reacted with a carboxylic acid orthoester. The remainder of the water is reacted with acetal.") This method has problems in that a carboxylic acid orthoester (which is an expensive compound) is used as a dehydrating agent, and methyl acetate is known to be by-produced (see "Kagaku Sochi (Chemical Equipment)", Vol. 41, No. 2, 52-54 (1999)). Thus, this method is as defective as the above-mentioned method.

Further, there has been proposed a method in which a large amount of an acetal compound is used as an organic dehydrating agent (see German Patent No. 4310109). There is also a patent document in which it is described that an acetal and carbon dioxide are reacted with each other by using, as a catalyst, a metal alkoxide or dibutyltin oxide (see Unexamined Japanese Patent Application Laid-Open Specification No. 2001-31629). (With respect to the reaction described in the latter, as a result of recent studies in the art, it is generally presumed that the actual reaction route is as follows. "An alcohol and carbon dioxide are reacted with each other to obtain a carbonic ester and water. The water is then reacted with an acetal.") However, these patent documents do not teach or suggest a method for producing an acetal compound in high yield without forming a waste. Further, the methods disclosed in these patent documents have a problem in that, when an acetal compound is used as a dehydrating agent, large amounts of by-products, such as a ketone and an aldehyde, are formed as wastes.

The effects aimed at by the methods which employ an organic dehydrating agent are to improve the number of turnovers of a catalyst. However, an organic dehydrating agent is consumed in a stoichiometric amount in accordance with the formation of a carbonic ester (and water as a by-product), so that a large amount of an organic dehydrating agent is consumed, thus forming a large amount of a degeneration product of the organic dehydrating agent. Therefore, it is necessary to perform an additional step of regenerating a large amount of a degenerated organic dehydrating agent. Further, in spite of the use of an organic dehydrating agent, the possibility still remains that deactivation of a catalyst occurs. The reason is as follows. In the conventional method for producing a carbonic ester by using the equilibrium reaction of the above-mentioned formula (3), carbon dioxide is in a supercritical state and, hence, the reaction is performed in supercritical carbon dioxide. In general, in supercritical carbon dioxide, a catalyst exhibits poor solubility, and the catalyst particles are likely to cohere together.

Therefore, there is a problem in that, when an organotin compound (which is susceptive to polymerization) is used as a catalyst in supercritical carbon dioxide, the organotin compound as a catalyst is likely to be deactivated due to its polymerization.

There has also been proposed a method which employs a solid dehydrating agent (see Applied Catalysts Vol. 142, L1-L3 (1996)). However, this method has a problem in that the solid dehydrating agent cannot be regenerated, thus forming a large amount of a waste.

There is also known a method in which an alcohol (methanol) and carbon dioxide are reacted with each other in the presence of a metal oxide (dibutyltin oxide) to thereby obtain a reaction mixture, and the obtained reaction mixture is cooled and introduced into a packed column containing a solid dehydrating agent, thereby gradually displacing the equilibrium toward a carbonic ester while effecting dehydration, to obtain a carbonic ester (see Unexamined Japanese Patent Application Laid-Open Specification No. 2001-247519). This method is based on a technique in which a conventional technique of using a dehydrating agent is combined with the known phenomenon that the water adsorbability of a conventional dehydrating agent (such as a molecular sieve) exhibits a temperature dependency. A dehydrating agent (such as a molecular sieve) exhibits lower water adsorbability at high temperatures than at low temperatures. Therefore, for removing a trace amount of water (by-product) from a reaction mixture which contains a largely excess amount of a low molecular weight alcohol used as a solvent, it is necessary to cool the reaction mixture in which an equilibrium is achieved under high temperature and pressure conditions, before introducing the reaction mixture into a packed column containing a solid dehydrating agent. In addition, for increasing the conversion of an alcohol as a raw material, it is necessary that the reaction mixture which has been cooled and dehydrated in the packed column be returned to high temperature and pressure conditions which are necessary for the reaction. Thus, this method has problems in that it is necessary to consume an extremely large amount of energy for cooling and heating, and a large amount of a solid dehydrating agent is needed. This method is very widely used for producing an aliphatic ester having a relatively large equilibrium constant. However, in the production of a carbonic ester from carbon dioxide and an alcohol, wherein the equilibrium of the reaction is largely biased toward the original system, this method cannot be suitably used because this method poses a serious problem that it is necessary to repeat the above-mentioned operation which needs a very large consumption of energy for cooling and heating. Further, for regenerating a degenerated dehydrating agent which has adsorbed water to saturation, it is generally necessary to calcine the degenerated dehydrating agent at several hundreds° C., thus rendering this method commercially disadvantageous. Furthermore, in this method, only one (water) of the two products of an equilibrium reaction is removed and, therefore, there is a problem in that, when the equilibrium reaction progresses to increase the carbonic ester concentration of the reaction system, the reaction becomes unlikely to progress any more, that is, this method is still under the restriction of an equilibrium reaction. In addition, dibutyltin oxide, which is used as a catalyst in this method, exhibits an extremely poor solubility in methanol and, hence, almost all of dibutyltin oxide as a catalyst remains in solid form in the reaction mixture. Therefore, when the reaction mixture is cooled to room temperature in a cooling step, the reaction mixture turns into a white slurry, thus causing a problem in that, in a subsequent dehydration step performed using a packed column containing a dehydrating agent, the slurry causes clogging of the packed column.

In general, a dehydration method in which water is removed by distillation is well-known in the field of organic synthesis reactions. However, in the field of the production of a carbonic ester from carbon dioxide and an alcohol, although "Study Report of Asahi Glass Association for Promotion of Industrial Technology (Asahi Garasu Kogyogijutsu Shoreikai Kenkyu Hokoku)", Vol. 33, 31-45 (1978) states that "dehydration by distillation is now being studied", there have been no reports or the like which state that a dehydration method using distillation has been completed. The reason why dehydration by distillation has not been performed in the art is, for example, that it is known that, when distillation under heating is performed, a reverse reaction occurs, causing a loss of a carbonic ester (see "Journal of the Chemical Society of Japan (Nippon Kagaku Kaishi)", No. 10, 1789-1794 (1975)). It is conceivable that, for lowering the heating temperature for distillation, the distillation is performed under reduced pressure. However, in the field of the distillation engineering, it is a common knowledge that it is difficult to completely remove a trace amount of water, by simple distillation, from a solvent having a hydrophilic group, such as an alcohol. Therefore, as dehydration methods, no dehydration method is known other than those methods using a large amount of an organic dehydrating agent or a large amount of a solid dehydrating agent. That is, all known dehydration methods have problems in that a large amount of a waste occurs, or a large consumption of energy is inevitable.

There has been a report which mentions a distillation separation of a carbonic ester from a reaction mixture containing a metal alkoxide, wherein the reaction mixture is obtained by reacting carbon dioxide and an alcohol with each other in the presence of a metal alkoxide catalyst; however, it is known in the art that, when a metal alkoxide catalyst is used, a distillation separation causes a reverse reaction, thus rendering it difficult to recover a carbonic ester by distillation separation (see "Journal of the Chemical Society of Japan (Nippon Kagaku Kaishi)", No. 10, 1789-1794 (1975)). Especially, no method is known by which a carbonic ester having a high boiling point can be separated in high yield from a reaction mixture containing a metal alkoxide.

A metal alkoxide is so unstable that it is susceptive to deactivation due to the moisture in the air. Therefore, the handling of a metal alkoxide needs strict care. For this reason, no conventional technique using a metal alkoxide catalyst has been employed in the commercial production of a carbonic ester. A metal alkoxide catalyst is an expensive compound, and no technique is known for regenerating a deactivated metal alkoxide catalyst.

There has been proposed a method for producing a carbonic ester by using a dibutyltin dialkoxide as a catalyst, in which, during the reaction, the catalyst is formed from dibutyltin oxide (which is stable to moisture) added to the reaction system (see Japanese Patent No. 3128576). This method has a problem in that, although dibutyltin oxide which is charged into the reaction system is stable, the dibutyltin oxide is converted, during the reaction, into a dibutyltin dialkoxide, which is unstable. Therefore, this method cannot solve the above-mentioned problem of the instability of a metal alkoxide catalyst. Further, for converting dibutyltin oxide into a dibutyltin dialkoxide in a reaction system, the reaction system needs to be placed under high temperature and pressure conditions. The reason for this is as follows. When an alkoxide is formed from dibutyltin oxide, water is generated, and the water needs to be consumed by hydrolysis of an acetal. However, tin exhibits only a very weak acidity, so that high temperature and pressure conditions are necessary for catalyzing the above-mentioned hydrolysis of an acetal.

Thus, in the conventional methods for producing a carbonic ester by using a metal alkoxide, carbon dioxide and an alcohol, when the metal alkoxide (which is expensive) has lost its catalyst activity due to hydrolysis or the like, there is no way to easily and effectively regenerate and reuse the metal alkoxide. Therefore, the conventional methods for producing a carbonic ester is disadvantageous in that it is necessary to use a large amount of an organic dehydrating agent or a solid dehydrating agent in combination with a small amount of a metal alkoxide.

As described hereinabove, the prior art techniques for producing a carbonic ester have many problems and, therefore, have not been put to practical use.

SUMMARY OF THE INVENTION

In this situation, the present inventors have made extensive and intensive studies with a view toward solving the above-mentioned problems of the prior art. As a result, it has unexpectedly been found that a carbonic ester can be produced in high yield by a method using a reaction route in which an organometal compound having a metal-oxygen-carbon linkage is used in a large amount as a precursor of a carbonic ester but not as a catalyst, and the organometal compound is subjected to an addition reaction with carbon dioxide to form an adduct, followed by a thermal decomposition reaction of the adduct, to thereby obtain a reaction mixture containing a carbonic ester. Further, the present inventors have also found that, by performing a subsequent operation in which the carbonic ester is separated from the reaction mixture to obtain a residual liquid, followed by a reaction of the residual liquid with an alcohol, there can be formed an organometal compound having a metal-oxygen-carbon linkage and water, wherein the water can be easily separated from the organometal compound by distillation or the like. The obtained organometal compound can be recovered and recycled to the above-mentioned reaction route for producing a carbonic ester. Based on these findings, the present invention has been completed.

Accordingly, a primary object of the present invention is to provide a method by which commercial production of a carbonic ester in high yield can be conducted continuously and repeatedly many times as desired without occurrence of a waste derived from a catalyst and without the need for using a large amount of a dehydrating agent.

The foregoing and other objects, features and advantages of the present invention will be apparent from the following detailed description taken in connection with the accompanying drawings and the appended claims.

DETAILED DESCRIPTION OF THE INVENTION

Figure 1:
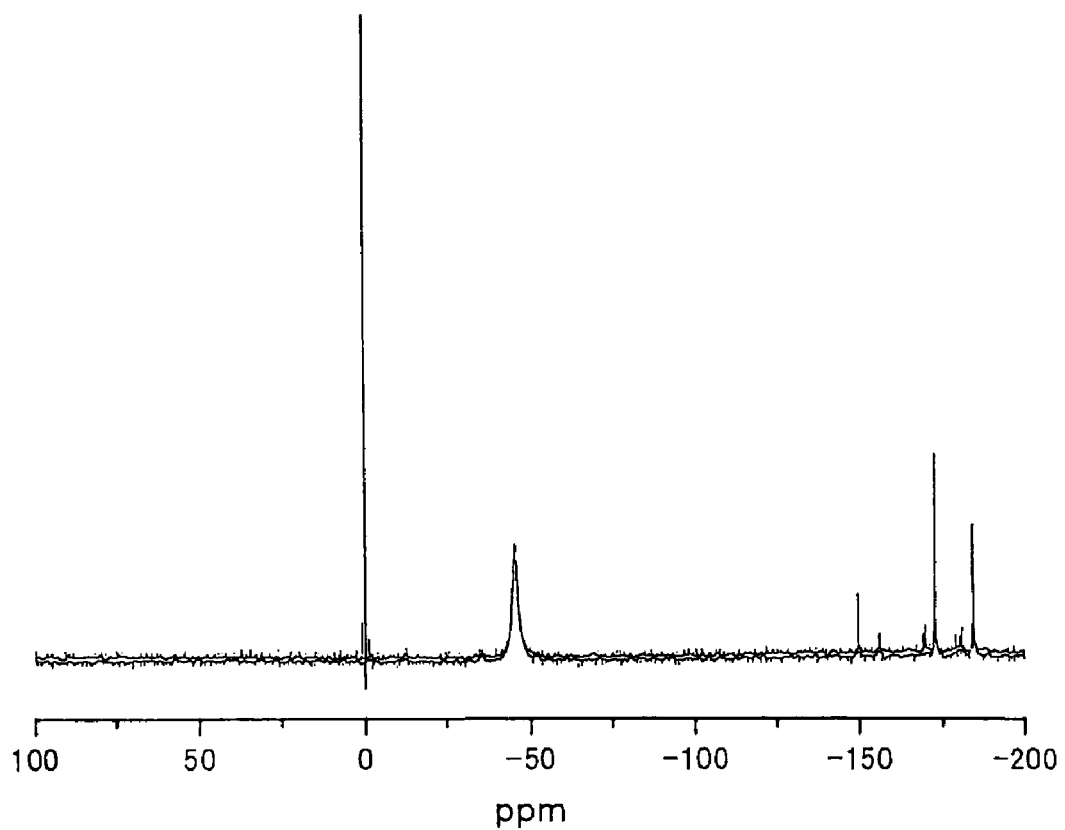
FIG. 1 is the $^{119}$Sn-NMR chart of the organometal compound having a 2-ethyl-1-hexyloxy group used in step (1) of the reaction in Example 1.

In the present invention, there is provided a method for producing a carbonic ester, comprising:

(1) performing a reaction between an organometal compound having a metal-oxygen-carbon linkage and carbon dioxide to obtain a reaction mixture containing a carbonic ester formed by the reaction, (2) separating the carbonic ester from the reaction mixture to obtain a residual liquid, and (3) reacting the residual liquid with a first alcohol to form at least one organometal compound having a metal-oxygen-carbon linkage and form water and removing the water from the at least one organometal compound, wherein the at least one organometal compound obtained in step (3) is recovered for recycle thereof to step (1).

For easy understanding of the present invention, the essential features and various preferred embodiments of the present invention are enumerated below.

1. A method for producing a carbonic ester, comprising:
   (1) performing a reaction between an organometal compound having a metal-oxygen-carbon linkage and carbon dioxide to obtain a reaction mixture containing a carbonic ester formed by the reaction,
   (2) separating the carbonic ester from the reaction mixture to obtain a residual liquid, and
   (3) reacting the residual liquid with a first alcohol to form at least one organometal compound having a metal-oxygen-carbon linkage and form water and removing the water from the at least one organometal compound, wherein the at least one organometal compound obtained in step (3) is recovered for recycle thereof to step (1).

2. The method according to item 1 above, wherein, in step (1), the organometal compound is used in an amount which is $\frac{1}{50}$ to 1 time the stoichiometric amount relative to the amount of the carbon dioxide.

3. The method according to item 2 above, wherein the reaction in step (1) is performed at 20° C. or more.

4. The method according to item 1 above, wherein the organometal compound used in step (1) comprises at least one compound selected from the group consisting of:
   an organometal compound represented by the formula (1):

(1)

wherein:
   $M^1$ represents a metal atom selected from the group consisting of elements belonging to Groups 4 and 14 of the Periodic Table, exclusive of silicon;
   each of $R^1$ and $R^2$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;
   each of $R^3$ and $R^4$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and
   each of a and b is an integer of from 0 to 2, a+b=0 to 2, each of c and d is an integer of from 0 to 4, and a+b+c+d=4; and
an organometal compound represented by the formula (2):

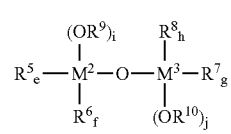

(2)

wherein:
   each of $M^2$ and $M^3$ independently represents a metal atom selected from the group consisting of elements belonging to Groups 4 and 14 of the Periodic Table, exclusive of silicon;
   each of $R^5$, $R^6$, $R^7$ and $R^8$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;
   each of $R^9$ and $R^{10}$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and
   e+f=0 to 2, g+h=0 to 2, each of i and j is independently an integer of from 1 to 3, e+f+i=3, and g+h+j=3.

5. The method according to item 1 above, wherein the reaction in step (1) is performed in the presence of a second alcohol which is the same as or different from the first alcohol used in step (3).

6. The method according to item 1 above, wherein the separation of the carbonic ester in step (2) is performed in the presence of a third alcohol which is the same as or different from the first alcohol used in step (3).

7. The method according to item 1 above, wherein the separation of the carbonic ester in step (2) is performed by at least one separation method selected from the group consisting of distillation, extraction and filtration.

8. The method according to item 1 above, wherein the removal of the water in step (3) is performed by membrane separation.
9. The method according to item 8 above, wherein the membrane separation is pervaporation.
10. The method according to item 1 above, wherein the removal of the water in step (3) is performed by distillation.
11. The method according to item 1 above, wherein the first alcohol used in step (3) is at least one alcohol selected from the group consisting of an alkyl alcohol having a straight chain or branched $C_1$-$C_{12}$ alkyl group, a cycloalkyl alcohol having a $C_5$-$C_{12}$ cycloalkyl group, an alkenyl alcohol having a straight chain or branched $C_2$-$C_{12}$ alkenyl group, and an aralkyl alcohol having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl.
12. The method according to item 11 above, wherein each of the alkyl alcohol, the cycloalkyl alcohol, the alkenyl alcohol and the aralkyl alcohol has a boiling point which is higher than the boiling point of water.
13. The method according to item 12 above, wherein the alkyl alcohol comprises at least one member selected from the group consisting of n-butyl alcohol, isobutyl alcohol and an alkyl alcohol having a straight chain or branched $C_5$-$C_{12}$ alkyl group, and the alkenyl alcohol has a straight chain or branched $C_4$-$C_{12}$ alkenyl group.
14. The method according to item 4 above, wherein each of $R^3$ and $R^4$ in formula (1) and $R^9$ and $R^{10}$ in formula (2) independently represents an n-butyl group, an isobutyl group, a straight chain or branched $C_5$-$C_{12}$ alkyl group, or a straight chain or branched $C_4$-$C_{12}$ alkenyl group.
15. The method according to item 4 or 14 above, wherein, in step (1), the organometal compound is used in at least one form selected from the group consisting of a monomeric form, an oligomeric form, a polymeric form and an associated form.
16. The method according to item 4 or 14 above, wherein each of $M^1$ in formula (1) and $M^2$ and $M^3$ in formula (2) represents a tin atom.
17. The method according to any one of items 1 to 16 above, which further comprises, after step (3), a step (4) in which the at least one organometal compound recovered in step (3) is recycled to step (1), followed by repeating of a sequence of steps (1) to (4) one or more times.
18. The method according to item 17 above, wherein the organometal compound used in step (1) is produced from an organotin oxide and an alcohol.

Hereinbelow, the present invention is described in detail.

As described above, the conventional methods for producing a carbonic ester employs an equilibrium reaction represented by the following formula (3):

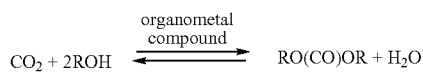

(R Represents an Unsaturated or Saturated Hydrocarbon Group)

That is, as the conventional methods, there can be mentioned a method in which a dehydrating agent is used for a reaction mixture containing the equilibrium reaction system (represented by the formula (3) above), wherein the equilibrium reaction system contains a product system comprising a carbonic ester and water; and a method in which a reaction mixture containing the above-mentioned equilibrium reaction system is cooled and subjected to a dehydration treatment in which the reaction mixture is introduced into a packed column containing a solid dehydrating agent, and circulated through the packed column, so as to gradually dehydrate the equilibrium reaction system to thereby suppress a decomposition reaction of the catalyst and accumulate a carbonic ester being formed in a trace amount.

On the other hand, the technical concept of the method of the present invention is completely different from the technical concept of the conventional methods.

The method of the present invention is characterized in:

that a reaction route is used in which an organometal compound having a metal-oxygen-carbon linkage is used in a large amount as a precursor of a carbonic ester but not as a catalyst, and the organometal compound is subjected to an addition reaction with carbon dioxide to form an adduct, followed by a thermal decomposition reaction of the adduct, to thereby obtain a reaction mixture containing a carbonic ester (step (1)), that step (1) is followed by an operation in which the carbonic ester is separated from the reaction mixture to obtain a residual liquid (step (2)), and that step (2) is followed by a reaction of the residual liquid with an alcohol to thereby obtain a reaction mixture comprising an organometal compound having a metal-oxygen-carbon linkage and water, followed by removal of the water from the reaction mixture by distillation or the like, to thereby obtain the organometal compound, whereupon the obtained organometal compound is recovered (step (3)), followed by recycling thereof to step (1) for producing a carbonic ester.

The reaction in step (1) of the method of the present invention is represented by the below-mentioned formula (4). The reaction in step (3) of the method of the present invention is represented by the below-mentioned formula (5).

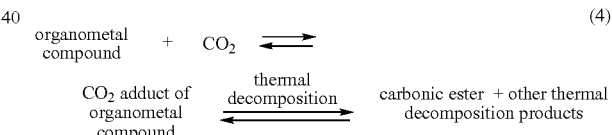

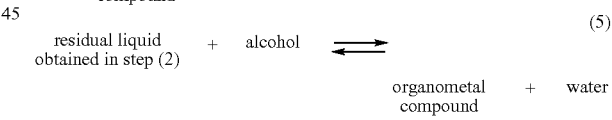

Thus, the method of the present invention is a method in which an organometal compound having a metal-oxygen-carbon linkage is used mainly as a precursor of a carbonic ester, and the organometal compound is subjected to an addition reaction with carbon dioxide to form an adduct, followed by a thermal decomposition reaction of the adduct, to thereby obtain a reaction mixture containing a carbonic ester, whereupon the carbonic ester is separated from the reaction mixture to obtain a residual liquid, followed by an operation in which the residual liquid (containing a metamorphic organometal compound formed by the thermal decomposition reaction of the adduct) is reacted with an alcohol to thereby regenerate an organometal compound having a metal-oxygen-carbon linkage. The regenerated organometal compound is recovered and recycled to the step of producing a carbonic ester, and the cycle of these steps is repeated so as to obtain a carbonic ester in a desired amount.

The reaction mixture obtained by step (1) of the method of the present invention may or may not contain a residual part of the organometal compound having a metal-oxygen-carbon linkage used in step (1). Also, the residual liquid obtained by step (2) of the method of the present invention may or may not contain a residual part of the organometal compound having a metal-oxygen-carbon linkage used in step (1). Anyway, an organometal compound having a metal-oxygen-carbon linkage is regenerated (resynthesized) before completion of step (3).

In the conventional methods using the equilibrium reaction of the formula (3) above, the entire reaction is held under equilibrium. By contrast, in the method of the present invention, the equilibrium reaction of the formula (3) above can be effectively divided into consecutive reactions which can be easily controlled, thereby rendering it possible to efficiently produce a carbonic ester while separating a carbonic ester and water from the reaction system. Specifically, in step (1) of the method of the present invention, a reaction can be performed in the absence of water. In step (2) of the method of the present invention, a reverse reaction of a carbonic ester and other thermal decomposition products can be prevented by separating a carbonic ester from the reaction mixture. In step (3) of the method of the present invention, after the regeneration of an organometal compound having a metal-oxygen-carbon linkage, the organometal compound can be recovered by removing water. Further, in each step of the method of the present invention, the operation conditions can be easily optimized by appropriately employing conventional techniques of chemical synthesis, such as cooling, heating, stirring, pressurizing and decompression.

As an example of an organometal compound having a metal-oxygen-carbon linkage used in step (1) of the method of the present invention, there can be mentioned an organometal compound having an alkoxy group. It is preferred that the organometal compound used in step (1) comprises at least one compound selected from the group consisting of:

an organometal compound represented by the formula (1):

wherein:

$M^1$ represents a metal atom selected from the group consisting of elements belonging to Groups 4 and 14 of the Periodic Table, exclusive of silicon;

each of $R^1$ and $R^2$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^3$ and $R^4$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of a and b is an integer of from 0 to 2, a+b=0 to 2, each of c and d is an integer of from 0 to 4, and a+b+c+d=4; and an organometal compound represented by the formula (2):

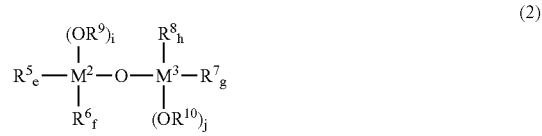

wherein:

each of $M^2$ and $M^3$ independently represents a metal atom selected from the group consisting of elements belonging to Groups 4 and 14 of the Periodic Table, exclusive of silicon;

each of $R^5$, $R^6$, $R^7$ and $R^8$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^9$ and $R^{10}$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and e+f=0 to 2, g+h=0 to 2, each of i and j is independently an integer of from 1 to 3, e+f+i=3, and g+h+j=3.

The Periodic Table mentioned herein is as prescribed in the IUPAC (International Union of Pure and Applied Chemistry) nomenclature system (1989).

The above-mentioned organometal compound is used in at least one form selected from the group consisting of a monomeric form, an oligomeric form, a polymeric form and an associated form.

Each of $M^1$ in the formula (1) and $M^2$ and $M^3$ in the formula (2) independently represents a metal atom selected from the group consisting of elements belonging to Groups 4 and 14 of the Periodic Table, exclusive of silicon. It is preferred that each of $M^1$, $M^2$ and $M^3$ is a metal atom selected from the group consisting of a titanium atom, a tin atom and a zirconium atom. From the viewpoint of the solubility in and reactivity with an alcohol, it is more preferred that each of $M^1$, $M^2$ and $M^3$ is a tin atom.

Examples of $R^1$ and $R^2$ in the formula (1) and $R^5$, $R^6$, $R^7$ and $R^8$ in the formula (2) include $C_1$-$C_{12}$ aliphatic hydrocarbon groups and $C_5$-$C_{12}$ alicyclic hydrocarbon groups, such as a methyl group, an ethyl group, an n-propyl group, an isopropyl group, an n-butyl group, an isobutyl group, a 2-butenyl group, a pentyl group, a hexyl group, a cyclopropyl group, a cyclobutyl group, a cyclopentyl group, a cyclopentadienyl group, a cyclohexyl group and a cyclohexenyl group; $C_7$-$C_{20}$ aralkyl groups, such as a benzyl group and a phenylethyl group; and $C_6$-$C_{20}$ aryl groups, such as a phenyl group, a tolyl group and a naphthyl group. $R^1$, $R^2$, $R^5$, $R^6$, $R^7$ and $R^8$ are not limited to these examples. Of the above-mentioned groups, lower alkyl groups are preferred and straight chain or branched $C_1$-$C_4$ alkyl groups are more preferred. Groups having more carbon atoms than mentioned above can be used as $R^1$, $R^2$, $R^5$, $R^6$, $R^7$ and $R^8$; however, when such groups having a larger number of carbon atoms are used, it is sometimes possible that the fluidity of the organometal compound and/or the productivity of a carbonic ester becomes low. Examples of $R^3$ and $R^4$ in the formula (1) and $R^9$ and $R^{10}$ in the formula (2) include $C_1$-$C_{12}$ aliphatic hydrocarbon groups and $C_5$-$C_{12}$ alicyclic hydrocarbon groups, such as a methyl group, an ethyl group, an n-propyl group, an isopropyl group, an n-butyl group, an isobutyl group, a 2-butenyl group, a pentyl group, a hexyl group, a cyclopropyl group, a cyclobutyl group, a cyclopentyl group, a cyclopentadienyl group, a cyclohexyl group, a cyclohexenyl group, a methoxyethyl group and an ethoxymethyl group; and $C_7$-$C_{20}$ aralkyl groups, such as a benzyl group and a phenylethyl group. $R^3$, $R^4$, $R^9$ and $R^{10}$ are not limited to these examples.

Examples of organometal compounds represented by formula (1) above include tetramethoxytin, tetraethoxytin, tetrapropyloxytin, tetrabutoxytin, tetrapentyloxytin, tetrahexyloxytin, tetrakis(2-ethyl-1-hexyloxy)tin, dimethoxydiethoxytin, tetramethyltitanate, tetraethyltitanate, tetrapropyltitanate, tetraisopropyltitanate, dimethyltin dimethoxide, dimethyltin diethoxide, 2-ethyl-1-hexyloxymethoxydimethyltin, dimethyltin dipropoxide, dimethyltin dibutoxide, dimethyltin bis(2-ethyl-1-butoxide), dimethyltin dipentyloxide, dimethyltin dihexyloxide, dimethyltin dicyclohexyloxide, dimethyltin bis(2-ethyl-1-hexyloxide), dimethyltindipropenyloxide, dimethyltin dibenzyloxide, methylbutyltin dimethoxide, methylbutyltin diethoxide, 2-ethyl-1-hexyloxymethoxymethylbutyltin, methylbutyltin dipropoxide, methylbutyltin dibutoxide, methylbutyltin bis(2-ethyl-1-butoxide), methylbutyltin dipentyloxide, methylbutyltin dihexyloxide, methylbutyltin dicyclohexyloxide, methylbutyltin bis(2-ethyl-1-hexyloxide), methylbutyltin dipropenyloxide, methylbutyltin dibenzyloxide, methyl(2-ethylhexyl)tin dimethoxide, methyl(2-ethylhexyl)tin diethoxide, 2-ethyl-1-hexyloxymethoxymethyl(2-ethylhexyl)tin, methyl(2-ethylhexyl)tin dipropoxide, methyl(2-ethylhexyl)tin di-butoxide, methyl(2-ethylhexyl)tin bis(2-ethyl-1-butoxide), methyl(2-ethylhexyl)tin dipentyloxide, methyl(2-ethylhexyl)tin dihexyloxide, methyl(2-ethyl-hexyl)tin dicyclohexyloxide, methyl(2-ethylhexyl)tin bis(2-ethyl-1-hexyloxide), methyl(2-ethylhexyl)tin di-properiyloxide, methyl(2-ethylhexyl)tin dibenzyloxide, butyl(2-ethylhexyl)tin dimethoxide, butyl(2-ethyl-hexyl)tin diethoxide, 2-ethyl-1-hexyloxymethoxy butyl(2-ethylhexyl)tin, butyl(2-ethylhexyl)tin dipropoxide, butyl(2-ethylhexyl)tin dibutoxide, butyl(2-ethylhexyl)tin bis (2-ethyl-1-butoxide), butyl(2-ethyl-hexyl)tin dipentyloxide, butyl(2-ethylhexyl)tin dihexyloxide, butyl(2-ethylhexyl)tin dicyclohexyloxide, butyl(2-ethylhexyl)tin bis(2-ethyl-1-hexyloxide), butyl(2-ethylhexyl)tin dipropenyloxide, butyl (2-ethyl-hexyl)tin dibenzyloxide, di(n-butyl)tin dimethoxide, di(n-butyltin) diethoxide, 2-ethyl-1-hexyloxymethoxy di(n-butyl)tin, di(n-butyltin) dipropoxide, di(n-butyl)tin dibutoxide, di(n-butyl)tin bis(2-ethyl-1 -butoxide), di(n-butyl)tin dipentyloxide, di(n-butyl)tin dihexyloxide, di(n-butyl) tin dicyclohexyloxide, di(n-butyl)tin bis(2-ethyl-1-hexyloxide), di(n-butyl)tin di-propenyloxide, di(n-butyl)tin dibenzyloxide, di(t-butyl)tin dimethoxide, di(t-butyl)tin diethoxide, di(t-butyl)tin dipropoxide, di(t-butyl)tin dibutoxide, di(t-butyl)tin dipentyloxide, di(t-butyl)tin dihexyloxide, di(t-butyl)tin dicyclohexyloxide, di(t-butyl)tin di-propenyloxide, diphenyltin dimethoxide, diphenyltin diethoxide, diphenyltin dipropoxide, diphenyltin dibutoxide, diphenyltin bis(2-ethyl- 1 -butoxide), diphenyltin dipentyloxide, diphenyltin dihexyloxide, diphenyltin bis(2-ethyl- 1 -hexyloxide), diphenyltin dicyclohexyloxide, diphenyltin dipropenyloxide and diphenyltin dibenzyloxide.

Examples of organometal compounds represented by formula (2) above include alkoxydistannoxanes and aralkyloxydistannoxanes, such as 1,1,3,3-tetrabutyl-1,3-dimethoxydistannoxane, 1,1,3,3-tetrabutyl-1-methoxy-3-(2-ethyl-1-hexyloxy)distannoxane, 1,1,3,3-tetrabutyl-1,3-diethoxydistannoxane, 1,1,3,3-tetrabutyl-1,3-dibutoxydistannoxane, 1,1,3,3-tetrabutyl-1,3-bis(2-ethyl-1-butoxy)distannoxane, 1,1,3,3-tetrabutyl-1,3-dipropoxydistannoxane, 1,1,3,3-tetrabutyl-1,3-dipentyloxydistannoxane, 1,1,3,3-tetrabutyl-1,3-dihexyloxydistannoxane, 1,1,3,3-tetrabutyl-1,3-bis(2-ethyl-1-hexyloxy)distannoxane, 1,1,3,3-tetrabutyl-1,3-dicyclohexyloxydistannoxane, 1,1,3,3-tetrabutyl-1,3-dibenzyloxydistannoxane, 1,1,3,3-tetraphenyl-1,3-dimethoxydistannoxane, 1,1,3,3-tetraphenyl-1,3-diethoxydistannoxane, 1,1,3,3-tetraphenyl-1,3-dibutoxydistannoxane, 1,1,3,3-tetraphenyl-1,3-bis(2-ethyl-1-butoxy)distannoxane, 1,1,3,3-tetraphenyl-1,3-dipropoxydistannoxane, 1,1,3,3-tetraphenyl-1,3-dipentyloxydistannoxane, 1,1,3,3-tetraphenyl-1,3-dihexyloxydistannoxane, 1,1,3,3-tetraphenyl-1,3-bis(2-ethyl-1-hexyloxy)distannoxane and 1,1,3,3-tetraphenyl-1,3-dicyclohexyloxydistannoxane.

The above-mentioned organometal compounds may be used individually or in combination. Further, orgnometal compounds other than those mentioned above may be used in combination with those mentioned above. As an organometal compound, those organometal compounds which are commercially available may be used. Alternatively, organometal compounds represented by formula (1) above may be obtained by a conventional method (e.g., a method described in Dutch Patent No. 6612421) in which dibutyltin oxide, an alcohol having 4 or more carbon atoms and a solvent exhibiting an azeotropy with water are mixed together to effect a reaction, and the resultant is subjected to distillation, thereby obtaining a fraction containing an organometal compound represented by formula (1) above. The above-mentioned patent document (i.e., Dutch Patent No. 6612421) describes that this method cannot be employed for obtaining an organometal compound having a $C_1$-$C_3$ alkoxy group and that an organometal compound having a $C_1$-$C_3$ alkoxy group can be obtained from dibutyltin chloride and sodium alcoholate. On the other hand, as a result of the studies by the present inventors, it has been found that, by employing a method described in Japanese Patent Application No. 2001-396537 and Japanese Patent Application No. 2001-396545, there can be obtained an organometal compound represented by formula (1) or (2) from a metal oxide and an alcohol. By this method, there can be obtained an organometal compound having a $C_1$-$C_3$ alkoxy group, such as a methoxy group. For example, an organometal compound having a methoxy group can be obtained from dibutyltin oxide, methanol and hexane. It is known that, in such a case, methanol and hexane form a minimum boiling azeotrope. However, the present inventors have unexpectedly found that, by this method, the removal of water can be performed, even though the methanol/hexane mixture has a boiling point lower than that of water. Based on this finding, the present inventors have developed a method for producing an organometal compound from an alcohol having a boiling point lower than that of water. An organometal compound obtained from dibutyltin oxide and an alcohol having a boiling point lower than that of water tends to be comprised mainly of an organometal compound represented by formula (2). However, when it is desired to obtain a large amount of an organometal compound represented by formula (1), it can be achieved by subjecting the above-mentioned organometal compound comprised mainly of an organometal compound represented by formula (2) to distillation, to thereby obtain a fraction comprising an organometal compound represented by formula (1).

In the method of the present invention, the removal of water in step (3) can be performed by any conventional dehydration method which is generally employed in the art. The removal of water may be performed by, for example, the use of a solid dehydrating agent (e.g., molecular sieves), distillation, or membrane separation. However, when it is desired to obtain a large amount of an organometal compound in a short period of time, it is preferred that the removal of water is performed by distillation. The distillation may be performed by any conventional distillation method, such as atmospheric pressure distillation, vacuum distillation, superatmospheric pressure distillation, thin film distillation or extractive distillation. The distillation can be performed at a temperature of from −20° C. to the boiling point of the first alcohol used in step (3), preferably from 50° C. to the boiling point of the first alcohol used in step (3). Before or during the distillation, any desired substance may be added to the reaction mixture.

In step (1) of the method of the present invention, a second alcohol may be optionally used. (With respect to the purpose of the use of a second alcohol, explanation is made below.) When it is intended to use a second alcohol in step (1), there can be mentioned an operation in which, before step (1), an alcohol is used for producing an organometal compound of formula (1) and/or an organometal compound of (2), and a subsequent distillation for removing water from the resultant reaction mixture is performed so that a part of the alcohol remains in the distillation residue containing the organometal compound. In this way, an organometal compound for use in step (1) can be obtained in the form of a mixture thereof with an alcohol which can be used as at least a part of a second alcohol in step (1). In this case, it becomes possible to perform step (1) without further adding an alcohol as a second alcohol.

In the method of the present invention, a first alcohol is used in step (3). In addition, a second alcohol may be optionally used in step (1) and a third alcohol may be optionally used in step (2). The first, second and third alcohols are the same or different. Examples of such alcohols include alkyl alcohols having a straight chain or branched $C_1$-$C_{12}$ alkyl group, cycloalkyl alcohols having a $C_5$-$C_{12}$ cycloalkyl group, alkenyl alcohols having a straight chain or branched $C_2$-$C_{12}$ alkenyl group, and aralkyl alcohols having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloakyl. Specific examples of these alcohols include $C_1$-$C_{12}$ aliphatic alcohols, such as methanol, ethanol, propanol, 2-propanol, n-butanol, 2-butanol, 2-ethyl-1-butanol, t-butanol, pentanol, hexanol, 2-ethyl-1-hexanol and hexenol; $C_5$-$C_{12}$ alicyclic alcohols, such as cyclopropanol, cyclobutanol, cyclopentanol, cyclohexanol and cyclohexenol; and aralkyl alcohols, such as benzyl alcohol and phenethyl alcohol. Further, as the first, second and third alcohols, polyhydric alcohols may be used. Examples of polyhydric alcohols include $C_1$-$C_{12}$ aliphatic polyhydric alcohols, such as ethylene glycol, 1,3-propanediol and 1,2-propanediol; $C_5$-$C_{12}$ alicyclic polyhydric alcohols, such as cyclohexanediol and cyclopentanediol; and aralkyl alcohols, such as benzenedimethanol.

Among the above-mentioned alcohols, preferred are $C_1$-$C_8$ primary or secondary monohydric alcohols, such as methanol, ethanol, propanol, 2-propanol, butanol, 2-butanol, 2-ethyl-1-butanol, pentanol, hexanol, 2-ethyl-1-hexanol, cyclohexanol and hexenol; and $C_7$-$C_8$ primary or secondary aralkyl alcohols, such as benzyl alcohol.

The organometal compounds which are, respectively, represented by formulae (1) and (2) can be analyzed by $^{119}$Sn-NMR Nuclear Magnetic Resonance ($^{119}$Sn-NMR) spectroscopy (see, for example, U.S. Pat. No. 5,545,600). However, in a $^{119}$Sn-NMR spectrum, a chemical shift value ascribed to the structure of the organometal compound represented by formula (1) largely varies depending, for example, on the organometal compound content of the sample used for a $^{119}$Sn-NMR analysis and on the presence or absence of an alcohol in the sample used for a $^{119}$Sn-NMR analysis. Therefore, it is preferred that the analysis of the organometal compound is performed by a method in which the proton nuclear magnetic resonance ($^1$H-NMR) spectroscopy and the carbon-13 nuclear magnetic resonance ($^{13}$C-NMR) spectroscopy are used in combination with the $^{119}$Sn-NMR spectroscopy. Table 1 below shows $^{119}$Sn-NMR data of examples of chemical shift values ascribed to the structure of an orgnometal compound represented by formula (1), which is produced from 2-ethyl-1-hexanol and dibutyltin oxide.

TABLE 1

Contents of an organometal compound of formula (1) having a 2-ethyl-1-hexyloxy group in sample solutions, and $^{119}$Sn-NMR chemical shift values obtained with respect to the sample solutions $^{119}$Sn-NMR data

| Organometal compound content (wt %) | Chemical shift value (δ ppm) |
|---|---|
| 48.0 | −64.2 |
| 20.5 | −19.1 |
| 11.2 | −6.6 |
| 3.4 | 2.7 |

Notes:
the chemical shift values (δ) are relative to that of tetramethyltin (SnMe$_4$).
The organometal compound content is the weight percentage (wt %) of organometal compound in deuterated chloroform (CDCl$_3$).

In the method of the present invention, the reaction system used in step (1) may contain substances other than those mentioned above. Examples of other substances which are effective in performing step (1) include those which function as a dehydrating agent in the reaction system. By using a dehydrating agent in step (1), the reaction system can be maintained under non-aqueous conditions. As a dehydrating agent, any conventional dehydrating agent may be used. Examples of dehydrating agents include acetal compounds and orthoesters, such as orthotrimethyl acetate. Further, organic dehydrating agents, such as dicyclohexylcarbodiimide may be used as dehydrating agents. Furthermore, solid dehydrating agents, such as molecular sieves, may be used as dehydrating agents. When a solid dehydrating agent is used, it is preferred that the solid dehydrating agent is removed from the reaction system prior to performing step (3).

In step (1) of the method of the present invention, the use of a second alcohol is optional. With respect to the amount of the second alcohol used in step (1), when an alcohol having an organic group which is the same as the alkoxy or aralkoxy group in the organometal compound is used as a second alcohol, from the viewpoint of improving the purity of the obtained carbonic ester, it is preferred that the second alcohol is used in an amount which is 1 to 100,000 times the stoichiometric amount relative to the amount of the organometal compound. Alternatively, when an alcohol having an organic group different from the alkoxy or aralkoxy group in the organometal compound is used as a second alcohol, or when the organometal compound represented by formula (2) is used alone, the amount of the second alcohol is preferably from 2 to 1,000 times the stoichiometric amount, more preferably from 10 to 1,000 times the stoichiometric amount, relative to the amount of the organometal compound. In step (1), when an alcohol having an organic group different from the organic group in the organometal compound is used as a second alcohol, an asymmetric carbon ester is obtained. As mentioned below, when a second alcohol is used in step (1), especially in the case where the organometal compound represented by formula (2) is used alone, the yield of the carbonic ester is greatly improved. The above-mentioned preferred amount of the second alcohol in the case where the organometal compound represented by formula (2) is used alone, is determined from this viewpoint.

In the case where step (3) is followed by step (4) (for recycling the organometal compound recovered in step (3) to step (1)) and step (1), prior to step (1), a second alcohol may be added to the reaction system so that the amount of the second alcohol becomes within the above-mentioned preferred range. Alternatively, in such case where step (3) is followed by step (4) and step (1), prior to step (1), an alcohol may be removed from the reaction system.

With respect to each step of the method of the present invention, detailed explanations are made hereinbelow.

Step (1) of the method of the present invention involves a reaction route in which a carbon dioxide adduct of an organometal compound having a metal-oxygen-carbon linkage is formed, and the adduct formed is thermally decomposed to obtain a carbonic ester. That is, in the reaction route of step (1), carbon dioxide is addition-bonded to an organometal compound to form an adduct, and the adduct is thermally decomposed. Differing from the conventional methods, step (1) of the method of the present invention is characterized in that an organometal compound having a metal-oxygen-carbon linkage is reacted with a small stoichiometric amount of carbon dioxide. In the conventional methods, carbon dioxide under a high pressure is reacted with an alcohol in the presence of a small amount of a metal catalyst. As an example of such conventional method, there can be mentioned a method in which carbon dioxide is reacted with methanol in the presence of dibutyltin dimethoxide (see Polyhedron, 19, pages 573-576 (2000)). In the conventional method described in this literature, carbon dioxide under a pressure of about 30 MPa is reacted with methanol at 180° C. in the presence of several millimoles of dibutyltin dimethoxide. The exact amount of carbon dioxide used in the reaction is not described in the above-mentioned literature. However, it is considered that, even if the partial pressure of methanol is subtracted, the amount of carbon dioxide used in the reaction should be as large as at least 100 times the stoichiometric amount relative to the amount of the organometal compound having a metal-oxygen-carbon linkage. By achieving the above-mentioned high pressure conditions, the equilibrium is forcibly displaced toward a carbonic ester, so that a carbonic ester can be produced in a yield which is higher than expected from the amount of the catalyst. However, by the reaction of carbon dioxide with methanol, free water is also produced, thus posing a serious problem in that the catalyst is hydrolyzed by the free water. For solving this problem, it is necessary to develop a method for dehydrating the reaction system. In the above-mentioned literature, it is described that, under the above-mentioned reaction conditions, dibutyltin oxide is produced as a hydrolysis product of dibutyltin dimethoxide, and that, although dibutyltin oxide cannot be dissolved in a solvent at room temperature, dibutyltin oxide is present in the form of a transparent solution under the above-mentioned reaction conditions. On the other hand, in the method of the present invention, even when the reaction mixture after completion of step (1) is cooled to room temperature, the reaction mixture generally remains in the form of a liquid. In this respect, the reaction used in the method of the present invention differs from the reaction used in the above-mentioned conventional method in which a large amount of carbon dioxide is used. In the case of the conventional method, the reaction system has a high carbon dioxide concentration and, hence, the reaction is necessarily performed under high pressure conditions. Therefore, when the reaction mixture containing the produced carbonic ester is taken out from the reactor, it is necessary to purge a large amount of carbon dioxide from the reactor before taking out the reaction mixture. Such necessity poses problems not only in that a large amount of carbon dioxide is wasted, but also in that, if it is intended to reuse the purged carbon dioxide, repressurization of the carbon dioxide becomes necessary and, hence, a large amount of energy is consumed for the repressurization of the carbon dioxide. Further, in the conventional method, the following problem is also likely to occur. It is known that, when the reaction system has a high carbon dioxide concentration, the density of the carbon dioxide gas layer increases, so that the carbon dioxide dissolves not only a solvent and a catalyst but also the produced carbonic ester, thereby forming a reaction mixture comprised of a homogeneous mixture of carbon dioxide, the solvent, the catalyst and the produced carbonic ester. When the reaction mixture (homogeneous mixture) is cooled to obtain a liquid reaction mixture, the liquid reaction mixture contains carbon dioxide in the form of liquid carbonic acid. Thus, anyway, it is extremely difficult to separate the produced carbonic ester from the reaction mixture.

In step (1) of the method of the present invention, it is preferred that carbon dioxide is used in an amount which is 1 to 50 times, more advantageously 1 to 20 times, as large as the stoichiometric amount relative to the amount of the organometal compound having a metal-oxygen-carbon linkage. When the amount of carbon dioxide is large, the reaction becomes a high pressure reaction, so that not only does it become necessary to use a reactor having high pressure resistance, but also a large amount of carbon dioxide is wasted during purging of unreacted carbon dioxide after completion of step (1). Therefore, it is still more preferred that carbon dioxide is used in an amount which is 1 to 10 times as large as the stoichiometric amount relative to the amount of the organometal compound. In other words, in step (1), it is preferred that the organometal compound is used in an amount which is $\frac{1}{50}$ to 1 time, more advantageously $\frac{1}{20}$ to 1 time, still more advantageously $\frac{1}{10}$ to 1 time, as large as the stoichiometric amount relative to the amount of carbon dioxide. In the present invention, a carbon dioxide adduct of the organometal compound having a metal-oxygen-carbon linkage can be easily obtained by contacting the organometal compound with carbon dioxide. When the reaction temperature is room temperature (20° C.), the carbon dioxide adduct is exothermically produced by contacting the organometal compound with a stream of carbon dioxide having atmospheric pressure. In this case, the carbon dioxide adduct can be obtained in a yield of almost 100%. In accordance with the elevation of the reaction temperature, the amount of the carbon dioxide adduct produced becomes lowered; however, even when the reaction temperature is high, the lowering of the amount of the carbon dioxide adduct can be suppressed by contacting the organometal compound with carbon dioxide having a high pressure. In step (1), when the organometal compound is contacted with carbon dioxide having a high pressure, it is difficult to determine the amount of the carbon dioxide adduct produced; however, it is preferred that the reaction of the organometal compound with carbon dioxide is conducted under a desired pressure, depending on the rate at which the carbonic ester is produced and on the amount of the carbonic ester produced. The reaction pressure is generally from atmospheric pressure to 200 MPa. It is preferred that the amount of the carbonic ester obtained in step (1) is 100% or less, more advantageously 50% or less, based on the stoichiometric mount relative to the amount of the organometal compound having a metal-oxygen-carbon linkage. The reason for this is as follows. The organometal compound having a metal-oxygen-carbon linkage used in the method of the present invention is more susceptible to hydrolysis than the carbonic ester produced. Therefore, when the carbonic ester is obtained in an amount which is 100% or less, preferably 50% or less, based on the stoichiometric amount relative to the amount of the organometal compound, water which is likely to hydrolyze the produced carbonic ester does advantageously not occur in the reaction mixture. On the other hand, in the case of the conventional methods, the reaction is conducted so that the amount of the carbonic ester produced is more than 100%, based on the stoichiometric amount relative to the amount of the organometal compound. As a result, in the case of the conventional methods, the generation of free water which is likely to hydrolyze the produced carbonic ester poses a serious problem. For preventing the produced carbonic ester from being hydrolyzed, it is necessary to add a dehydrating agent to the reaction system or to perform the reaction in the presence of a dehydrating agent, wherein the dehydrating agent is selected from the group consisting of a dehydrating agent which is more susceptible to hydrolysis than the organometal compound, and a solid dehydrating agent having high water adsorptivity. Such use of a dehydrating agent is disadvantageous not only in that a complicated step is needed, but also in that the dehydrating agent is expensive. Therefore, the conventional methods have not been practically employed as a method for producing a carbonic ester on a commercial scale. By contrast, in the reaction route of step (1) of the method of the present invention, the main reaction is a decomposition reaction in which a carbon dioxide adduct of the organometal compound having a metal-oxygen-carbon linkage is thermally decomposed to obtain a carbonic ester. The thermal decomposition reaction is performed at a temperature in the range of from 20 to 300° C. In step (1) of the method of the present invention, an alcohol exchange reaction or an ester exchange reaction may be performed together with the above-mentioned decomposition reaction. Specifically, for example, when step (1) is performed in the presence of a second alcohol, an alcohol exchange reaction occurs between an oxygen-carbon linkage of the second alcohol and an oxygen-carbon linkage of the organometal compound having a metal-oxygen-carbon linkage, so that a carbonic ester corresponding to the second alcohol can be obtained. Alternatively, after the formation of a carbonic ester, a second alcohol may be added to the reaction system to perform an ester exchange reaction, thereby obtaining another carbonic ester corresponding to the second alcohol.

With respect to step (1), more detailed explanations are made hereinbelow.

The studies by the present inventors have shown that in step (1), a carbonic ester is obtained by the reaction between the organometal compound and carbon dioxide. Therefore, the use of a second alcohol in step (1) is optional. However, from the viewpoint of producing a carbonic ester in high yield, it is preferred to use a second alcohol in step (1). The reason for this is as follows. The thermal decomposition reaction in step (1) has a reverse reaction. When a second alcohol is added to the reaction system, it is possible that another equilibrium reaction additionally occurs between the second alcohol and a thermal decomposition product other than the carbonic ester, thereby improving the yield of the carbonic ester. The addition of a second alcohol for improving the yield of the carbonic ester is especially effective when the organometal compound is comprised mainly of an organometal compound represented by formula (2). On the other hand, when the organometal compound is comprised mainly of an organometal compound represented by formula (1), the equilibrium of the thermal decomposition reaction in step (1) is biased toward the product system and, hence, the yield of the carbonic ester is considerably high, so that, in some cases, the yield of the carbonic ester cannot be further improved by the addition of a second alcohol. When the second alcohol contains a large amount of water, the yield of the carbonic ester is lowered. Therefore, it is preferred that the amount of water contained in the second alcohol is not more than 0.1 time, more advantageously not more than 0.01 time, as large as the stoichiometric amount relative to the amount of the organometal compound. When the reaction in step (1) is performed using an organometal compound represented by formula (1), a carbon dioxide adduct of the organometal compound represented by formula (1) is thermally decomposed to produce a carbonic ester. It is well known that a carbonic ester is produced from a dimer of the organometal compound represented by formula (1) (see ECO INDUSTRY, Vol. 6, No. 6, pages 11-18 (2001)). In the conventional method described in this literature, a carbonic ester as well as dibutyltin oxide is produced from a dimer of the organometal compound represented by formula (1), wherein the amount of the carbonic ester produced is two molecules per molecule of the dimer of the organometal compound. The present inventors have made extensive and intensive studies on the formation of a carbonic ester from an organometal compound. As a result, it has surprisingly been found that, when a carbon dioxide adduct of a dimer of the organometal compound represented by formula (1) is thermally decomposed, a carbonic ester is swiftly eliminated wherein the amount of the carbonic ester eliminated is one molecule per molecule of the carbon dioxide adduct, so that an organometal compound represented by formula (2) and/or a carbon dioxide adduct thereof can be obtained. In this case, addition of an alcohol is not necessary. Step (2) may be conducted immediately after there are obtained a carbonic ester and at least one compound selected from the group consisting of an organometal compound represented by formula (2) and a carbon dioxide adduct thereof. Alternatively, step (2) may be conducted after a carbonic ester is further produced from the obtained organometal compound represented by formula (2) and/or the obtained carbon dioxide adduct thereof. As mentioned above, it is preferred that the organometal compound used in step (1) comprises at least one compound selected from the group consisting of organometal compounds respectively represented by formulae (1) and (2). It is more preferred that at least a part of the organometal compound used in step (1) is an organometal compound represented by formula (1). It is still more preferred that the organometal compound used in step (1) contains 5 mol % or more of an organometal compound represented by formula (1), wherein the amount of the organometal compound is expressed in terms of the amount of a metal atom contained in the organometal compound.

A solvent for the organometal compound may be added to the reaction system used in step (1). The organometal compound used in the present invention is generally in the form of a liquid. However, in some cases, the organometal compound is in the form of a solid. Further, there is a case where the organometal compound turns into a solid form when the organometal compound becomes a carbon dioxide adduct thereof in step (1). Such a phenomenon occurs, for example, when dibutyltin dimethoxide is used as the organometal compound. Even when the organometal compound is in the form of a solid, a carbonic ester can be produced in step (1). However, the fluidity of the organometal compound is sometimes important when the carbonic ester is continuously produced. Further, for improving the rate of the reaction between the organometal compound and carbon dioxide, it is sometimes preferred that the organometal compound is in the form of a liquid. In such cases, step (1) may be conducted using a solvent for the organometal compound. As a solvent, there can be used an alcohol having the same organic group as in the carbonic ester produced. Alternatively, an inert solvent can also be used. Examples of inert solvents include hydrocarbons and ethers. Specific examples of inert solvents include $C_5$-$C_{20}$ saturated hydrocarbons, such as pentane, hexane, cyclohexane, heptane, octane and decane; $C_6$-$C_{20}$ aromatic hydrocarbons (which may have a $C_1$-$C_{14}$ saturated alkyl group and/or a $C_5$-$C_{14}$ cycloalkyl group), such as benzene, toluene, xylene and ethylbenzene; $C_6$-$C_{20}$ saturated alkyl ethers, such as dipropyl ether, dibutyl ether and dihexyl ether; $C_4$-$C_{20}$ cycloalkyl ethers, such as tetrahydrofuran and dioxane; and $C_7$-$C_{28}$ phenyl ethers (comprising a phenyl group having a $C_0$-$C_8$ substituent group, and a group selected from the group consisting of a $C_1$-$C_{14}$ alkyl group and a $C_5$-$C_{14}$ cycloalkyl group), such as anisole, ethyl phenyl ether, isopropyl phenyl ether, benzyl methyl ether and 4-methyl anisole.

Figure 4:
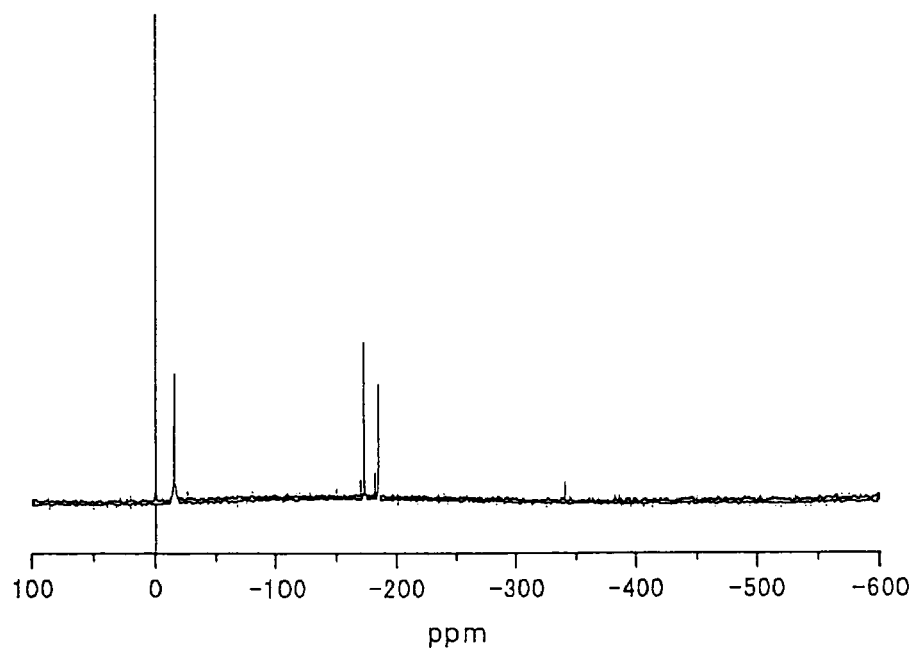
FIG. 4 is the $^{119}$Sn-NMR chart of the organometal compound having a 2-ethyl-1-hexyloxy group used in step (1) of the reaction in Example 3.
Figure 5:
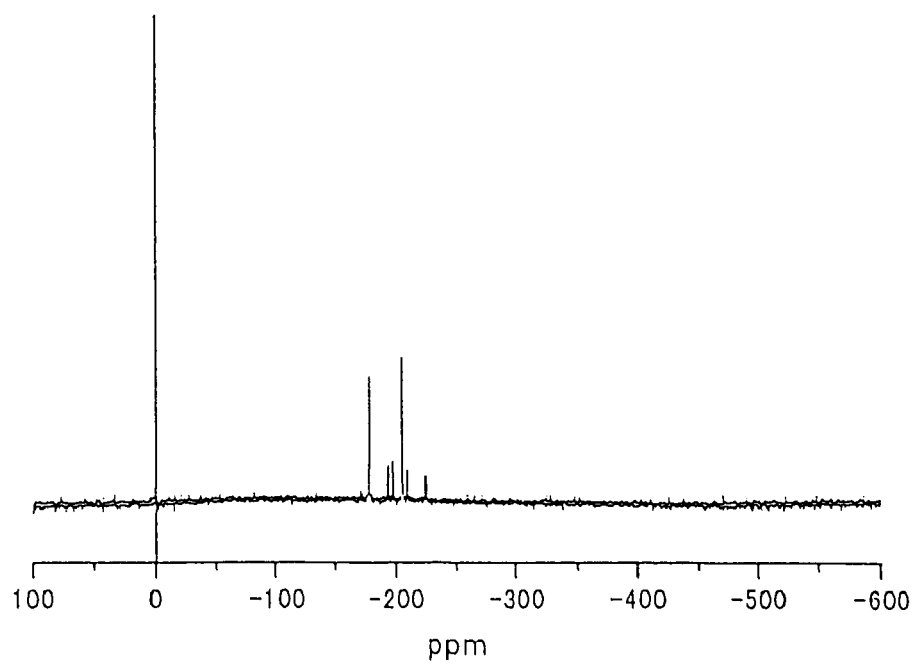
FIG. 5 is the $^{119}$Sn-NMR chart of the organometal compound obtained just after step (1) of the reaction in Example 3.

The temperature employed for the reaction performed in step (1) is generally in the range of from room temperature (20° C.) to 300° C. When it is intended to complete the reaction in a short period of time, it is preferred to perform the reaction at 80 to 200° C. for 10 minutes to 500 hours. When the organometal compound has a tin atom as a metal atom, there is a great difference between the state of the tin atom contained in the organometal compound before the reaction in step (1) and the state of the tin atom contained in the reaction mixture after step (1). This can be seen from a comparison between the $^{119}$Sn-NMR chart (see FIG. 4) obtained with respect to the organometal compound before the reaction in step (1) and the $^{119}$Sn-NMR chart (see FIG. 5) obtained with respect to the reaction mixture after step (1), and therefore it is apparent that the organometal compound functions as a precursor of the carbonic ester. FIG. 5 shows that, when both an organometal compound represented by formula (1) and an organometal compound represented by formula (2) are used in step (1), the organometal compound represented by formula (1) is consumed in step (1). The $^{119}$Sn-NMR chart shown in FIG. 5 exhibits a peak ascribed to the organometal compound represented by formula (2) and a peak which is presumed to be ascribed to a carbon dioxide adduct of the organometal compound represented by formula (2).

When the reaction in step (1) is performed at a high temperature (e.g., at 200° C. or more), the $^{119}$Sn-NMR chart obtained with respect to the reaction mixture after step (1) sometimes exhibits a peak ascribed to a certain substance around 100 ppm, wherein tetramethyltin is used as a reference in the $^{119}$Sn-NMR analysis. However, when the method of the present invention is repeatedly performed, it is preferred that the reaction in step (1) is performed under conditions wherein the formation of the above-mentioned substance exhibiting a peak around 100 ppm can be suppressed, or the reaction in step (1) is performed using an additive for suppressing the formation of the above-mentioned substance exhibiting a peak around 100 ppm.

With respect to the amount of carbon dioxide, when the reaction in step (1) is performed at room temperature (20° C.), it suffices if is used in an amount which is the stoichiometric amount relative to the amount of the organometal compound used in step (1). However, when the reaction in step (1) is performed at a temperature which is higher than room temperature (20° C.) under conditions wherein the amount of carbon dioxide is the stoichiometric amount relative to the amount of the organometal compound used in step (1), the rate of the addition bonding of carbon dioxide to the organometal compound sometimes becomes very low, so that the rate of the formation of the carbonic ester is markedly lowered. The pressure employed for the reaction performed in step (1) is generally from atmospheric pressure to 200 MPa, preferably from atmospheric pressure to 100 MPa, wherein, if desired, the reaction may be performed while introducing additional carbon dioxide into the reaction system or withdrawing a part of carbon dioxide from the reaction system. The introduction of additional carbon dioxide into the reaction system may be conducted either intermittently or continuously.

When it is confirmed by the analysis of the reaction mixture that a desired carbonic ester has been obtained, step (1) is finished. For example, when the carbonic ester is obtained in an amount which is 5% or less, based on the stoichiometric amount relative to the amount of the organometal compound, step (1) may be finished. The reaction mixture may be taken out from the reactor, either after the pressure in the reactor is reduced to atmospheric pressure, or without lowering the pressure in the reactor. When step (1), step (2) and step (3) are performed in separate reactors, the reaction mixture may be continuously circulated by, for example, a method in which the reaction mixture after step (3) is fed to the reactor for step (1); the reaction mixture contained in the reactor for step (1) is fed to the reactor for step (2); and the reaction mixture contained in the reactor for step (2) is fed to the reactor for step (3). The circulation of the reaction mixture is preferred from the viewpoint of reducing the amount of carbon dioxide purged from the reactor (for step (1)) which has carbon dioxide filled therein. The reaction mixture obtained at completion of each step may be cooled or heated. When the reaction mixture is cooled, the reaction mixture may be forcibly cooled or allowed to cool spontaneously. As described below, if desired, step (1) for synthesizing a carbonic ester and step (2) for separating the synthesized carbonic ester can be simultaneously performed.

Step (2) of the method of the present invention is a step in which the carbonic ester is separated from the reaction mixture obtained in step (1). As described above, in the production of a carbonic ester from carbon dioxide and an alcohol by a conventional method using the reaction of formula (3), water as well as a carbonic ester is formed, and the water is contacted with an adsorbent or a dehydrating agent to remove the water from the reaction system, thereby displacing the equilibrium of the reaction toward the product system. Theoretically, the amount of a carbonic ester produced can also be increased by continuously removing the produced carbonic ester from the reaction system so as to displace the equilibrium of the reaction toward the product system. However, in the conventional method, when the produced carbonic ester is removed from the reaction system, water produced by the reaction is accumulated in the reaction system. As is well known in the art, if water is accumulated in the reaction system, the catalyst is hydrolyzed by the water and loses its catalyst activity. The hydrolyzed catalyst has very poor solubility in the solvent and, hence, poses a problem in that, in a subsequent dehydration step performed using an adsorption column, the hydrolyzed catalyst causes clogging of the adsorption column. Further, there has not been a method for regenerating the catalyst which has lost its catalyst activity by the hydrolysis thereof. For this reason, in the conventional methods, it has been impossible to efficiently separate the produced carbonic ester from the reaction mixture.

In step (2) of the method of the present invention, a conventional method for separating the carbonic ester from the reaction mixture can be used. For example, the separation of the carbonic ester from the reaction mixture can be conducted by any of solvent extraction, distillation and membrane filtration, each of which is well known in the art. As a preferred example of an extraction solvent, there can be mentioned a solvent having no reactivity to the carbonic ester. Examples of such solvents include aliphatic and alicyclic hydrocarbons, such as hexane and cyclohexane; halogenated hydrocarbons, such as chloroform, dichloromethane and trichloromethylene; aromatic hydrocarbons, such as benzene, toluene and chlorobenzene; and ethers, such as diethyl ether and anisole.

When an alcohol having four or less carbon atoms is used as a second alcohol in step (1), or when a second alcohol is not used in step (1) and the organometal compound has an organic group having four or less carbon atoms, the carbonic ester can be separated, by distillation, directly from the reaction mixture obtained in step (1). In this case, it is preferred that the carbonic ester produced is a carbonic ester (such as dimethyl carbonate or diethyl carbonate) having a boiling point of 100° C. or less. The distillation can be performed by any conventional method. For example, the distillation can be performed by any of a distillation under atmospheric pressure, a distillation under reduced pressure, a distillation under superatmospheric pressure, and a thin film distillation, each of which is well known in the art. The temperature for the distillation is generally from −20 to 200° C., preferably from −20 to 150° C. The distillation may be performed either in the presence of a solvent or by extractive distillation.

In step (2), if desired, a third alcohol may be used. When a third alcohol is added to the reaction system, an ester exchange reaction occurs between the carbonic ester obtained in step (1) and the third alcohol to thereby obtain a carbonic ester which has a different number of carbon atoms from that of the carbonic ester obtained in step (1), thereby rendering it easy to separate a carbonic ester from the reaction mixture. This method using a third alcohol is preferably employed when the carbonic ester obtained in step (1) has nine or more carbon atoms and the carbonic ester separated in step (2) has seven or less carbon atoms. This method is more preferably employed when the carbonic ester separated in step (2) is dimethyl carbonate. The amount of the third alcohol used in step (2) is 1 to 1,000 times the stoichiometric amount relative to the amount of the organometal compound used in step (1). The temperature employed for the ester exchange reaction is preferably in the range of from room temperature (about 20° C.) to 200° C. Taking into consideration the desired rate of the ester exchange reaction and the occurrence of a decomposition reaction of the carbonic ester at a high temperature, the temperature employed for the ester exchange reaction is more preferably in the range of from 50 to 150° C. In the ester exchange reaction, a conventional catalyst may be used. The ester exchange reaction and the separation of the carbonic ester from the reaction mixture may be conducted either in a batchwise manner or simultaneously. As a method for separating the carbonic ester from the reaction mixture after the ester exchange reaction, any of the above-mentioned separation methods (such as solvent extraction, distillation and membrane filtration) can be used. Most preferred is a reactive distillation in which the ester exchange and the separation of the carbonic from the reaction mixture are simultaneously conducted.

Before the separation of the carbonic ester from the reaction mixture by extraction, distillation or the like, the organometal compound remaining unreacted and a thermal decomposition product of the organometal compound may be removed from the reaction mixture. For example, the carbonic ester can be obtained by the following method. Water or a solvent containing water is added to the reaction mixture to thereby obtain a white slurry. Solids in the slurry are removed by filtration to obtain a filtrate. By subjecting the thus obtained filtrate to extraction, distillation or the like, the carbonic ester can be obtained in high recovery even when the carbonic ester has a boiling point of more than 100° C. The water used may be any type of water; however, it is preferred to use distilled water or deionized water.

The amount of water used in step (2) is generally 1 to 100 times the stoichiometric amount relative to the amount of the organometal compound used in step (1). The amount of water needed for separating the unreacted organometal compound from the reaction mixture by phase separation is at most 1 time as large as the stoichiometric amount relative to the amount of the organometal compound used in step (1). However, because the carbonic ester produced in step (1) is hydrophobic, it is preferred to add water to the reaction mixture in an amount which is several times as large as the stoichiometric amount relative to the amount of the organometal compound used in step (1), thereby enabling separation not only of the unreacted organometal compound but also of the carbonic ester from the reaction mixture by phase separation.

The temperature of water used in step (2) is a temperature at which the water is not solidified in the reaction mixture. Specifically, the temperature of water is generally in the range of from −20 to 100° C., preferably from 0 to 100° C., more preferably from 10 to 80° C. From the viewpoint of preventing the carbonic ester from being hydrolyzed, the temperature of water is still more preferably in the range of from 10 to 50° C. A solvent may or may not be used in combination with water. When a solvent is used in combination with water, it is preferred to use a solvent having no reactivity to the carbonic ester. In the case where a second alcohol is used in step (1), when water is used in the form of a solution thereof in an alcohol which is the same as the second alcohol used in step (1), the separation of the solvent from the reaction mixture becomes easy. When a third alcohol is used in step (2) for performing an ester exchange reaction, it is preferred that, after completion of the ester exchange reaction, water is added to the reaction mixture wherein the water is used in the form of a solution thereof in an alcohol which is the same as present in the reaction mixture.

The distillation of the reaction mixture can be conducted by any of a distillation under atmospheric pressure, a distillation under reduced pressure, a distillation under superatmospheric pressure, and a thin film distillation, each of which is well known in the art. The distillation can be conducted at a temperature of from −20° C. to the boiling point of the carbonic ester and/or alcohol, preferably from 50° C. to the boiling point of the carbonic ester and/or alcohol. The distillation may be performed either in the presence of a solvent or by extractive distillation.

If desired, the following operation may be conducted. To the reaction mixture after step (1) is added water and/or an extraction solvent to obtain a mixture having an oil phase which contains the carbonic ester. The oil phase is separated from the mixture, followed by recovery of the carbonic ester from the oil phase.

By the method of the present invention, not only a symmetric carbonic ester but also an asymmetric carbonic ester can be produced. In the case of the production of an asymmetric carbonic ester by using a conventional method, a symmetric carbonic ester is first produced, and the produced symmetric carbonic ester is then subjected to an ester exchange reaction to produce an asymmetric carbonic ester. On the other hand, in the method of the present invention, an asymmetric carbonic ester can be directly produced. Therefore, the method of the present invention is advantageous from the viewpoint of reducing the energy cost and reducing the facility construction cost. In the method of the present invention, an asymmetric carbonic ester can be produced as follows. Explanations are made below, taking as an example the case where the organometal compound has at least one type of alkoxy group. When the organometal compound used in step (1) has two different types of alkoxy groups, an asymmetric carbonic ester can be produced without use of alcohols (as a second alcohol and a third alcohol) in steps (1) and (2). On the other hand, when the organometal compound used in step (1) has only one type of alkoxy group, an asymmetric carbonic ester can be produced by conducting step (1) in the presence of an alcohol (second alcohol) having an organic group which is different from the alkoxy group of the organometal compound, or by conducting step (2) in the presence of an alcohol (third alcohol) having an organic group which is different from the alkoxy group of the organometal compound. Further, in each of the case where the organometal compound used in step (1) has only one type of alkoxy group and the case where the organometal compound used in step (1) has two different types of alkoxy groups, an asymmetric carbonic ester can also be produced by conducting step (1) in the presence of two different alcohols (second alcohols), or by conducting step (2) in the presence of two different alcohols (third alcohols). When two different alcohols are used, the stoichiometric ratio of the two alcohols varies depending on the types of the two alcohols; however, the stoichiometric ratio is generally in the range of from 2:8 to 8:2, wherein each of the amounts of the two alcohols is expressed in terms of the stoichiometric amount relative to the amount of the organometal compound. When it is intended to produce an asymmetric carbonic ester in a ratio which larger than that of a symmetric carbonic ester, it is preferred that the stoichiometric ratio of the two alcohols is as close to 1 as possible. Specifically, the stoichiometric ratio of the two alcohols is preferably in the range of from 3:7 to 7:3, more preferably in the range of from 4:6 to 6:4. When the production of an asymmetric carbonic ester is performed using two different alcohols which are used in excess amounts (for example, amounts each of which is at least 10 times the stoichiometric amount relative to the amount of the organometal compound), it becomes possible to obtain an asymmetric carbonic ester having two different types of alkoxy groups corresponding to the two alcohols, irrespective of the type of the alkoxy group of the organometal compound used in step (1). The separation of the asymmetric carbonic ester from the reaction mixture can be conducted by any of the methods (such as solvent extraction, distillation and membrane filtration) described above in connection with step (2). In many cases, not only an asymmetric carbonic ester but also a symmetric carbonic ester is produced. In such cases, the following operation may be conducted. The asymmetric and symmetric carbonic esters are separated from the reaction mixture to obtain a residual liquid. The asymmetric carbonic ester is separated from the symmetric carbonic ester. The symmetric carbonic ester is either mixed with the residual liquid, followed by step (3), or returned to step (1) or (2).

Step (3) is a step of synthesizing (regenerating) an organometal compound having a metal-oxygen-carbon linkage. A compound contained in the residual liquid obtained after the separation of the carbonic ester in step (2) is generally in the form of a transparent liquid, but sometimes in the form of a solid. Irrespective of the type of the form of the compound, the compound can be used in step (3) for forming an organometal compound. The compound in the residual liquid obtained after the separation of the carbonic ester in step (2) is generally in the form of a liquid. For example, the residual liquid does not contain dibutyltin oxide in the form of a solid (it should be noted that dibutyltin oxide has no solubility in almost all organic solvents at room temperature (20° C.) and, hence, is in the form of a solid under such conditions). The structure of the compound in the residual liquid has not yet been identified. However, it has surprisingly been found that, by performing the reaction in step (3) of the method of the present invention, there can be obtained an organometal compound having a metal-oxygen-carbon linkage, such as an organometal compound represented by formula (1) and/or an organometal compound represented by formula (2).

Step (3) comprises reacting the residual liquid obtained in step (2) with a first alcohol to form at least one organometal compound having a metal-oxygen-carbon linkage and form water and removing the water from the at least one organometal compound, wherein the at least one organometal compound obtained in step (3) is recovered for recycle thereof to step (1).

Examples of first alcohols used in step (3) include those which are exemplified above. Specific examples of first alcohols include $C_1$-$C_{12}$ aliphatic alcohols and $C_5$-$C_{12}$ alicyclic alcohols, such as methanol, ethanol, propanol, 2-propanol, n-butanol, 2-butanol, 2-ethyl-1-butanol, t-butanol, pentanol, hexanol, 2-ethyl-1-hexanol, hexenol, cyclopropanol, cyclobutanol, cyclopentanol, cyclohexanol and cyclohexenol; and aralkyl alcohols, such as benzyl alcohol and phenethyl alcohol. Also, polyhydric alcohols can be used as first alcohols. Examples of polyhydric alcohols include $C_1$-$C_{12}$ aliphatic polyhydric alcohols and $C_5$-$C_{12}$ alicyclic polyhydric alcohols, such as ethylene glycol, 1,3-propanediol, 1,2-propanediol, cyclohexanediol and cyclopentanediol; and aralkyl polyhydric alcohols, such as benzene dimethanol. If desired, prior to use of any of the above-mentioned alcohols, for example, distillation of the alcohol may be conducted for purifying the alcohol or adjusting the concentration of the alcohol. From this viewpoint, it is preferred to use an alcohol having a boiling point of 300° C. or less as measured under atmospheric pressure. From the viewpoint of the ease in the removal of water in step (3), it is more preferred to use at least one alcohol selected from the group consisting of n-butanol, isobutanol, an alkyl alcohol having five or more carbon atoms and an aralkyl alcohol having five or more carbon atoms.

With respect to the structure of an organometal compound obtained by using a polyhydric alcohol as a first alcohol in step (3), there is no particular limitation. For example, the organometal compound may be comprised of at least one member selected from the group consisting of a crosslinked product of an organometal compound represented by formula (1) and a crosslinked product of an organometal compound represented by formula (2).

The amount of the first alcohol used in step (3) is preferably 1 to 10,000 times, more preferably 2 to 100 times, the stoichiometric amount relative to the amount of the organometal compound used in step (1). When a sequence of steps (1) to (4) is repeated one or more times, it is sometimes possible that an alcohol is present in the residual liquid obtained by step (2). In such cases, an appropriate amount of an alcohol may be added to the residual liquid so that the amount of the alcohol in the residual liquid becomes within the above-mentioned range of the amount of the first alcohol. Alternatively, the alcohol present in the residual liquid may be removed.

The removal of water in step (3) can be performed by any conventional method. For example, the removal of water in step (3) can be performed by any of distillation, a method using a dehydration column filled with a solid dehydrating agent, and a method using membrane separation (such as pervaporation). Among them, distillation and a method using membrane separation (such as pervaporation) are preferred. It is well known that pervaporation can be used for the removal of water in an alcohol. In the present invention, pervaporation can be preferably used. In the case of an alcohol having a boiling point higher than that of water, the removal of water in the alcohol can also be easily performed by distillation under heating. On the other hand, in the case of an alcohol having a boiling point lower than that of water, the removal of water in the alcohol can also be performed by a distillation technique in which a solvent forming an azeotropic mixture with water is used.

The temperature employed for the reaction performed in step (3) varies depending on the type of the first alcohol used; however, the temperature is generally from room temperature (20° C.) to 300° C. When the removal of water in step (3) is performed by distillation, the temperature employed for the distillation is not particularly limited so long as water has a vapor pressure at the temperature. When it is intended to complete the reaction in step (3) in a short period of time under atmospheric pressure, it is preferred that the distillation is conducted under conditions wherein the temperature of the vapor formed by distillation is the azeotropic temperature of water and the first alcohol. When water and the first alcohol do not form an azeotropic mixture, it is preferred that the distillation is conducted at the boiling point of water. When it is intended to complete the reaction in step (3) in a shorter period of time, the distillation may be conducted, using an autoclave, at a temperature higher than the boiling point of the first alcohol or water while gradually removing water in the vapor phase. When the temperature employed for the reaction performed in step (3) is extremely high, it is sometimes possible that a thermal decomposition of the organometal compound occurs. In such cases, a liquid containing water may be removed by reduced pressure distillation or the like.

Even when the first alcohol does not form an azeotropic mixture with water, water can be removed by azeotropic distillation in which a solvent forming an azeotropic mixture with water is used. This method is preferred since water can be removed at a low temperature. Examples of solvents which form an azeotropic mixture with water include unsaturated and saturated hydrocarbons, such as hexane, benzene, toluene, xylene, naphthalene; ethers, such as anisole and 1,4-dioxane; and halogenated hydrocarbons, such as chloroform.

From the viewpoint of facilitating the separation of water from the azeotropic mixture after azeotropic distillation, it is preferred to use, as a solvent, an unsaturated or saturated hydrocarbon in which water has low solubility. When such a solvent is used, it is necessary to use the solvent in an amount such that water can be satisfactorily removed by azeotropic distillation. It is preferred to use a distillation column for the azeotropic distillation because the solvent can be recycled to the reaction system after separating the solvent from the azeotropic mixture in the distillation column and, hence, the amount of the solvent can be reduced to a relatively small one.

By performing the reaction in step (3), there can be obtained, for example, at least one organometal compound selected from the group consisting of an organometal compound represented by formula (1) and an organometal compound represented by formula (2).

When the reaction in step (3) reaches a stage where almost no water is generated, step (3) can be finished. When a sequence of steps (1) to (4) is repeated one or more times, the amount of the carbonic ester obtained in step (1) varies depending on the amount of water which is removed in step (3). Therefore, it is preferred that the amount of water removed in step (3) is as large as possible.

Generally, the amount of water removed in step (3) is 0.01 to 1 time as large as the amount of water produced by the reaction in step (3), wherein the amount of water produced is theoretically calculated based on the assumption that only an organometal compound represented by formula (1) is produced by the reaction in step (3). In many cases, the amount of water removed in step (3) is less than 1 time as large as the above-mentioned theoretical amount of water produced by the reaction in step (3). As a result of the studies made by the present inventors, it has been found that, when an organometal compound is produced from dibutyltin oxide and an alcohol and a sequence of steps (1) to (4) is repeated one or more times, the amount of water removed in step (3) is less than the amount of water generated during the reaction in which the organometal compound is produced from dibutyltin oxide and an alcohol. When, in step (2), water is added to the reaction system for separating the carbonic ester, it is sometimes possible that a white solid containing water is obtained and the amount of water removed in step (3) is more than 1 time the above-mentioned theoretical amount of water produced by the reaction in step (3). When a sequence of steps (1) to (4) is repeated one or more times, it is difficult to calculate a theoretical amount of water produced by the reaction performed in step (3) because the structure of the organometal compound obtained after step (2) has not yet been identified. In this case, the change (with time) in amount of water which is removed is measured. When it is confirmed by the measurement that almost no more water is removed, step (3) may be finished.

After completion of step (3), if desired, an excess amount of the alcohol may be removed. From the viewpoint of improving the purity of the carbonic ester obtained in step (1) in the case where a sequence of steps (1) to (4) is repeated one or more times, it is preferred to remove an excess amount of the alcohol. When the same alcohol as used in step (3) is used in step (1) in the case where a sequence of steps (1) to (4) is repeated one or more times, the removal of the alcohol after step (3) may not be performed. Further, an appropriate amount of the alcohol may be added to the reaction system after step (3).

The removal of an excess amount of the alcohol can be performed as follows. When the organometal compound obtained in step (3) is in the form of a solid, the alcohol can be removed as a filtrate obtained by filtration. On the other hand, when the organometal compound obtained in step (3) is in the form of a liquid, the removal of the alcohol can be performed by reduced pressure distillation, or by a method in which an inert gas, such as nitrogen, is introduced into the reactor so that the alcohol is removed in an amount which corresponds to the vapor pressure of the alcohol. In the case of using an inert gas, when the inert gas is not completely dried, a disadvantage is likely to occur wherein the organometal compound is hydrolyzed and decomposed into a metal oxide and an alcohol, so that the amount of the carbonic ester obtained by the reaction in step (1) in the case where a sequence of steps (1) to (4) is repeated one or more times, becomes extremely lowered. Steps (1) to (3) may be performed either continuously or in a batchwise manner.

As described above, if desired, steps (1) and (2) can be simultaneously performed. Also, if desired, steps (2) and (3) can be simultaneously performed. Further, steps (1) to (3) can also be simultaneously performed. With respect to such simultaneous performance of these steps, explanations are made hereinbelow.

(The Case where Steps (1) and (2) are Simultaneously Performed)

With respect to the reaction performed in step (1), there are two cases: one is the case where a liquid phase and a vapor phase are present during the performance of the reaction in step (1), and the other is the case where carbon dioxide is in a supercritical state under high temperature and high pressure conditions and the reaction mixture forms a homogeneous mixture. Steps (1) and (2) can be simultaneously performed in the case where a liquid phase and a vapor phase are present during the performance of the reaction in step (1). In this case, the reaction temperature and reaction pressure vary depending on the type of an alkoxy group contained in the organometal compound and the type of an alcohol when an alcohol is used. However, the reaction temperature is generally 200° C. or less and the reaction pressure is 8 MPa or less. The carbonic ester has high solubility in carbon dioxide and, hence, a part of the carbonic ester is dissolved in the vapor phase. Therefore, by performing the reaction in step (1) while withdrawing a part of the vapor phase, the carbonic ester can be separated from the reaction mixture.

(The Case where Steps (2) and (3) Are Simultaneously Performed)

Steps (2) and (3) can be simultaneously performed when the organometal compound is obtained from an alcohol having a boiling point higher than that of water, and a $C_1$-$C_3$ alkyl alcohol is used in step (1) or (2). The separation of the carbonic ester and water from the reaction mixture can be performed by a method in which the reaction mixture obtained in step (1) is placed under a stream of an inert gas, such as carbon dioxide, thereby removing the carbonic ester and water from the reaction mixture by entraining with the inert gas. The separation of the carbonic ester and water from the reaction mixture can also be performed by a conventional method, such as membrane separation. By such a method, the carbonic ester and water can be continuously separated from the reaction mixture.

(The Case where Steps (1) to (3) Are Simultaneously Performed)

With respect to the reaction performed in step (1), there are two cases: one is the case where a liquid phase and a vapor phase are present during the performance of the reaction in step (1), and the other is the case where carbon dioxide is in a supercritical state under high temperature and high pressure conditions and the reaction mixture forms a homogeneous mixture. Steps (1) to (3) can be simultaneously performed in the case where a liquid phase and a vapor phase are present during the performance of the reaction in step (1), the organometal compound is obtained from an alcohol having a boiling point higher than that of water, and a $C_1$-$C_3$ alkyl alcohol (preferably methanol) is used. In this case, the reaction temperature and reaction pressure vary depending on the type of an alkoxy group contained in the organometal compound and the type of an alcohol when an alcohol is used. However, the reaction temperature is generally 150° C. or less and the reaction pressure is generally 5 MPa or less. Water and the carbonic ester have high solubility in carbon dioxide and, hence, a part of the carbonic ester is dissolved in the vapor phase. Therefore, by performing the reaction in step (1) while withdrawing a part of the vapor phase, the carbonic ester can be separated from the reaction mixture while regenerating the organometal compound. Further, it is also possible to employ a method in which the reaction is performed in a fixed-bed reactor containing an organometal compound, wherein the organometal compound is supported on a carrier or in the form of a solid. In this method, carbon dioxide and a $C_1$-$C_3$ alcohol are introduced into the fixed-bed reactor to effect a reaction, thereby obtaining a carbonic ester and water in such a form as entrained by carbon dioxide gas. As a carrier for supporting the organometal compound, a conventional carrier can be used.

Step (4) is a step in which the at least one organometal compound recovered in step (3) is recycled to step (1). A sequence of steps (1) to (4) can be repeated one or more times. Prior to the recycle of the organometal compound to step (1), the organometal compound may be cooled or heated. The step (4) can be performed either continuously or in a batchwise manner.

BEST MODE FOR CARRYING THE INVENTION

Hereinbelow, the present invention will be described in more detail with reference to the following Examples and Comparative Examples, which should not be construed as limiting the scope of the present invention.

In the following Examples and Comparative Examples, various measurements and analyses were conducted by the following methods.

1) Nuclear Magnetic Resonance (NMR) Analysis of an Organometal Compound

Apparatus: JNM-A400 FT-NMR system (manufactured and sold by JEOL Ltd., Japan) (400 MHz)

(1) Preparation of Sample Solutions for $^1$H- and $^{13}$C-NMR Analyses

About 0.1 g to 0.5 g of an organometal compound was weighed, and then about 0.9 g of deuterated chloroform was added thereto, thereby obtaining a sample solution for an NMR analysis.

(2) Preparation of a Sample Solution for a $^{119}$Sn-NMR Analysis

About 0.1 to 1 g of a liquid containing an organometal compound was weighed, and then 0.05 g of tetramethyltin and about 0.85 g of deuterated chloroform were added thereto, thereby obtaining a sample solution for an NMR analysis.

2) Gas Chromatography (GC) Analysis of a Carbonic Ester

Apparatus: GC-2010 system (manufactured and sold by Shimadzu Corporation, Japan).

(1) Preparation of a Sample Solution 0.06 g of a liquid to be measured with respect to the carbonic ester content thereof was weighed, and then about 2.5 ml of dehydrated dimethylformamide or dehydrated acetonitrile was added thereto. Further, to the resultant was added about 0.06 g of diphenyl ether as an internal standard.

(2) Conditions for a GC Analysis

Column: DB-1 (manufactured and sold by J & W Scientific, U.S.A.)

Liquid phase: 100% dimethyl polysiloxane

Column length: 30 m

Column diameter: 0.25 mm

Film thickness: 1 μm

Column temperature: the temperature was elevated from 50° C. to 300° C. at a rate of 10° C./min.

Injection temperature: 300° C.
Detector temperature: 300° C.
Detector: FID (flame iozination detector)

(3) Quantitative Analysis

The quantitative analysis of a sample solution was conducted using a calibration curve obtained with respect to standard samples.

3) Calculation of the Yield of a Carbonic Ester

The yield of a carbonic ester was calculated by the following formula (6):

Yield of carbonic ester (%)=(stoichiometric amount of carbonic ester obtained)/(stoichiometric amount of organometal compound used in step (1))×100 (6)

Herein, the term "stoichiometric amount of organometal compound" means a value calculated by dividing the number of metal atoms of the organometal compound by Avogadro's number.

EXAMPLE 1

(Synthesis of an Organometal Compound Having a 2-ethyl-1-hexyloxy Group)

Into a 200-ml autoclave (manufactured and sold by Toyo Koatsu Co., Ltd., Japan) were charged 29 g (116 mmol) of dibutyltin oxide (manufactured and sold by Aldrich, U.S.A.) and 75 g (576 mmol) of 2-ethyl-1-hexanol (manufactured and sold by Aldrich, U.S.A.). The atmosphere in the autoclave was purged with nitrogen gas. Then, stirring of the contents of the autoclave was started, and the internal temperature of the autoclave was elevated to 192° C. A purge line was opened, and the stirring was continued for 3.5 hours under atmospheric pressure while distilling off water and 2-ethyl-1-hexanol. After that period, there was almost no distillate any more. Then, the inside of the autoclave was cooled to about 30° C. while purging the atmosphere in the autoclave with nitrogen gas, and there was obtained a reaction mixture containing an organometal compound having a 2-ethyl-1-hexyloxy group. The amount of the liquid (distillate) distilled off through the purge line during the reaction was about 50 g. The amount of water contained in the distillate was measured by the Karl Fischer method. It was found that the amount of water in the distillate was about 1.7 g. The $^{119}$Sn-NMR chart of the reaction mixture is shown in FIG. 1. As shown in FIG. 1, a peak ascribed to the organometal compound of formula (1) was detected at −45 ppm, and peaks ascribed to the organometal compound of formula (2) were, respectively, detected at −172 ppm and −184 ppm.

Step (1): Production of dimethyl carbonate from an organometal compound having a 2-ethyl-1-hexyloxy group, methanol and carbon dioxide gas Into the above-mentioned autoclave containing the reaction mixture was charged 75.5 g (2.4 mol) of methanol, and all valves were closed. Then, from a carbon dioxide gas bomb, carbon dioxide gas, the pressure of which was lowered to 5 MPa by means of a pressure regulator connected to the carbon dioxide gas bomb, was introduced into the autoclave. Stirring of the contents of the autoclave was started, and the internal temperature of the autoclave was elevated to 160° C. A liquid carbonic acid was gradually introduced through a feed line into the autoclave so as to adjust the internal pressure of the autoclave to 19.6 MPa. Then, a reaction was performed for 1 hour while maintaining the internal pressure of the autoclave at 19.6 MPa, thereby obtaining a reaction mixture, and the inside of the autoclave was cooled to about 30° C., followed by purging of the carbon dioxide gas.

Step (2): Isolation of dimethyl carbonate

In the above-mentioned autoclave, a vacuum distillation was performed at 30° C. under a pressure of 13 KPa, thereby separating dimethyl carbonate and methanol from the reaction mixture by distillation and recovering them through a distillate withdrawal line of the autoclave. Thus, dimethyl carbonate was obtained in a yield of 17%.

Step (3): Synthesis (regeneration) of an organometal compound 75 g (576 mmol) of 2-ethyl-1-hexanol (manufactured and sold by Aldrich, U.S.A.) was added to the residual liquid in the autoclave, obtained in step (2). The atmosphere in the autoclave was purged with nitrogen gas. Then, stirring of the contents of the autoclave was started, and the internal temperature of the autoclave was elevated to 192° C. The purge line was opened, and the stirring was continued for 3.5 hours under atmospheric pressure while distilling off water and 2-ethyl-1-hexanol. After that period, there was almost no distillate any more. Then, the inside of the autoclave was cooled to about 30° C. while purging the atmosphere in the autoclave with nitrogen gas, and there was obtained a reaction mixture containing an organometal compound having a 2-ethyl-1-hexyloxy group.

Step (4): Recycling of the organometal compound obtained in step (3) to step (1)

Subsequently, the same procedures as in step (1) and step (2) were successively performed as follows.

Step (1): Production of dimethyl carbonate from an organometal compound having a 2-ethyl-1-hexyloxy group, methanol and carbon dioxide gas Into the above-mentioned autoclave containing the reaction mixture was charged 75.5 g (2.4 mol) of methanol, and all valves were closed. Then, from a carbon dioxide gas bomb, carbon dioxide gas, the pressure of which was lowered to 5 MPa by means of a pressure regulator connected to the carbon dioxide gas bomb, was introduced into the autoclave. Stirring of the contents of the autoclave was started, and the internal temperature of the autoclave was elevated to 160° C. A liquid carbonic acid was gradually introduced through a feed line into the autoclave so as to adjust the internal pressure of the autoclave to 19.6 MPa. Then, a reaction was performed for 1 hour while maintaining the internal pressure of the autoclave at 19.6 MPa, thereby obtaining a reaction mixture, and the inside of the autoclave was cooled to about 30° C., followed by purging of the carbon dioxide gas.

Step (2): Isolation of dimethyl carbonate

In the above-mentioned autoclave, a vacuum distillation was performed at 30° C. under a pressure of 13 KPa, thereby separating dimethyl carbonate and methanol from the reaction mixture by distillation and recovering them through a distillate withdrawal line of the autoclave. Thus, dimethyl carbonate was obtained in a yield of 16%.

EXAMPLE 2

As described below, dimethyl carbonate was produced by performing a cycle of steps (1) to (4) 26 times consecutively.

(Synthesis of an Organometal Compound Having a Hexyloxy Group)

There was provided a 200-ml autoclave (manufactured and sold by Toyo Koatsu Co., Ltd., Japan) which had connected thereto a line for introducing a liquid carbonic acid and carbon dioxide gas, a distillate withdrawal line, a sampling tube and a line for introducing nitrogen gas into the bottom of the autoclave. Into the 200-ml autoclave were charged 15.0 g (60 mmol) of dibutyltin oxide (manufactured and sold by Aldrich, U.S.A.) and 30.7 g (300 mmol) of hexanol (manufactured and sold by Aldrich, U.S.A.; a dehydrated grade). The autoclave was sealed and all valves were closed. The atmosphere in the autoclave was purged 3 times with nitrogen gas. Then, stirring of the contents of the autoclave was started, and the internal temperature of the autoclave was elevated to 160° C. Then, the stirring was continued for 30 minutes. Thereafter, the valve of the distillate withdrawal line was opened, and recovery of a distillate was started and continued while blowing nitrogen gas into the bottom of the autoclave at a flow rate of 200 ml/minute. About 2 hours after the start of the recovery of a distillate, there was no distillate any more. Then, the inside of the autoclave was cooled to about 50° C., and there was obtained a transparent reaction mixture. A small amount of the reaction mixture was sampled and subjected to a $^{119}$Sn-NMR analysis. The $^{119}$Sn-NMR analysis confirmed that there were formed the organometal compound of formula (1) and the organometal compound of formula (2). The distillate exhibited a separation into two layers, and the amount of the water layer was about 0.9 ml.

Then, a cycle of the below-described steps (1) to (4) was repeated.

Step (1): Production of dimethyl carbonate from an organometal compound having a hexyloxy group, methanol and carbon dioxide gas Into the above-mentioned autoclave containing the reaction mixture was charged 48.1 g (1.5 mol) of methanol, and all valves were closed. Then, from a carbon dioxide gas bomb, carbon dioxide gas, the pressure of which was lowered to 5 MPa by means of a pressure regulator connected to the carbon dioxide gas bomb, was introduced into the autoclave. Stirring of the contents of the autoclave was started, and the internal temperature of the autoclave was elevated to 160° C. A liquid carbonic acid was gradually introduced through a feed line into the autoclave so as to adjust the internal pressure of the autoclave to 22 MPa. Then, a reaction was performed for 16 hours while maintaining the internal pressure of the autoclave at 22 MPa, thereby obtaining a reaction mixture, and the inside of the autoclave was cooled to about 30° C., followed by purging of the carbon dioxide gas.

Step (2): Isolation of dimethyl carbonate

In the above-mentioned autoclave, a vacuum distillation was performed at 30° C. under a pressure of 13 KPa, thereby separating dimethyl carbonate and methanol from the reaction mixture by distillation and recovering them through a distillate withdrawal line of the autoclave. Thus, dimethyl carbonate was obtained.

Step (3): Synthesis (regeneration) of an organometal compound

Into the above-mentioned autoclave was charged about 20 g of hexanol (manufactured and sold by Aldrich, U.S.A.; a dehydrated grade), and all valves were closed. The atmosphere in the autoclave was purged 3 times with nitrogen gas. Then, stirring of the contents of the autoclave was started, and the internal temperature of the autoclave was elevated to 160° C. Then, the stirring was continued for 30 minutes. Thereafter, the valve of the distillate withdrawal line was opened, and recovery of a distillate was started and continued while blowing nitrogen gas into the bottom of the autoclave at a flow rate of 200 ml/minute. About 2 hours after the start of the recovery of a distillate, the inside of the autoclave was cooled to about 50° C., and there was obtained a transparent reaction mixture.

Step (4): Recycling of the organometal compound obtained in step (3) to step (1)

The yield of dimethyl carbonate obtained in step (2) of each cycle is shown in Table 2.

TABLE 2

| Cycle No. of reaction | Yield (%) |
| --- | --- |
| 1 | 16.7 |
| 2 | 20.4 |
| 3 | 21.9 |
| 4 | 20.1 |
| 5 | 20.5 |
| 6 | 20.2 |
| 7 | 20.4 |
| 8 | 20.5 |
| 9 | 19.6 |
| 10 | 19.5 |
| 11 | 21.9 |
| 12 | 20.2 |
| 13 | 19.9 |
| 14 | 18.0 |
| 15 | 19.3 |
| 16 | 19.4 |
| 17 | 18.5 |
| 18 | 18.3 |
| 19 | 18.1 |
| 20 | 18.0 |
| 21 | 18.6 |
| 22 | 18.4 |
| 23 | 17.9 |
| 24 | 17.8 |
| 25 | 17.4 |
| 26 | 17.5 |

Figure 2:
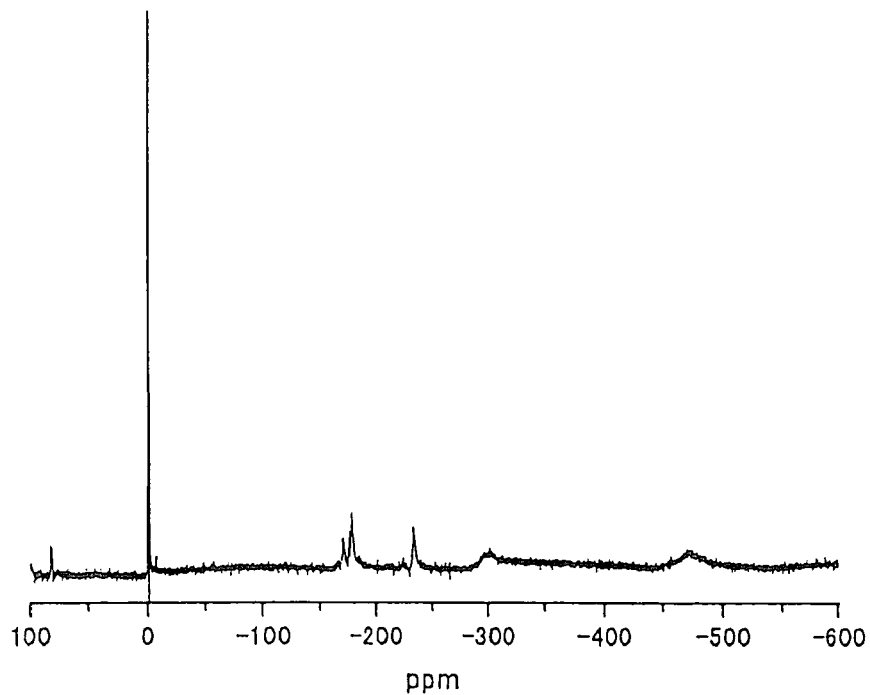
FIG. 2 is the $^{119}$Sn-NMR chart of the organometal compound obtained just after step (2) of the 26th cycle of reaction in Example 2.
Figure 3:
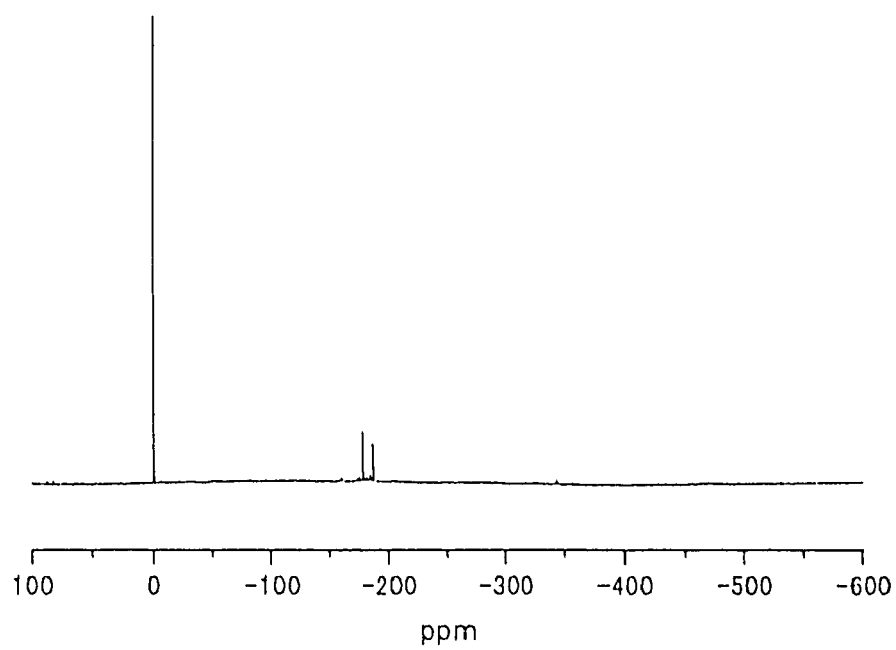
FIG. 3 is the $^{119}$Sn-NMR chart of the organometal compound obtained just after step (3) of the 26th cycle of reaction in Example 2.

After step (2) of the 26th cycle of reaction, the residual liquid obtained in step (2) was subjected to a $^{119}$Sn-NMR analysis. In the $^{119}$Sn-NMR chart of the residual liquid, several peaks were detected between −170 ppm and −500 ppm, in addition to a peak ascribed to a small amount of the organometal compound of formula (2) (see FIG. 2). After step (3) of the 26th cycle of reaction, the reaction mixture obtained in step (3) was subjected to a $^{119}$Sn-NMR analysis. In the $^{119}$Sn-NMR chart of the reaction mixture, a peak ascribed to the organometal compound of formula (2) was detected, and the above-mentioned several peaks between −170 ppm and −500 ppm were no longer detected (see FIG. 3).

The amounts of water distilled off in step (3)s of the 1st to 4th cycles of reaction were, respectively, 0.27 ml, 0.24 ml, 0.22 ml and 0.24 ml.

EXAMPLE 3

(Synthesis of an Organometal Compound Having a 2-ethyl-1-hexyloxy Group)

Into a 500-ml eggplant-shaped flask were charged 105 g (422 mmol) of dibutyltin oxide (manufactured and sold by Aldrich, U.S.A.) and 277 g (2.1 mol) of 2-ethyl-1-hexanol (manufactured and sold by Aldrich, U.S.A.). The eggplant-shaped flask was connected to a rotary evaporator (manufactured and sold by EYELA, Japan). The atmosphere in the eggplant-shaped flask was purged with nitrogen gas. Rotation of the eggplant-shaped flask in an oil bath was started, and the oil bath was heated to 180° C. During the heating, a white slurry in the eggplant-shaped flask turned into a transparent solution. Then, the rotation of the eggplant-shaped flask was continued for about 30 minutes. Thereafter, the internal pressure of the eggplant-shaped flask was gradually lowered from 80.7 KPa to 68.7 KPa over 3 hours by means of a vacuum pump (manufactured and sold by SATO VAC INC., Japan) and a vacuum controller (manufactured and sold by OKANO WORKS, LTD., Japan) while distilling off water and a small amount of 2-ethyl-1-hexanol. After that period, there was almost no distillate any more. Then, the inside of the flask was cooled to about 30° C. and the internal pressure of the flask was returned to atmospheric pressure by means of nitrogen gas, and there was obtained 310 g of a reaction mixture which was a transparent solution of an organometal compound having a 2-ethyl-1-hexyloxy group in 2-ethyl-1-hexanol. The $^{119}$Sn-NMR chart of the obtained transparent solution is shown in FIG. 4. As shown in FIG. 4, a peak ascribed to the organometal compound of formula (1) was detected at −14 ppm, and peaks ascribed to the organometal compound of formula (2) were, respectively, detected at −172 ppm and −184 ppm.

Step (1): Production of dimethyl carbonate from an organometal compound having a 2-ethyl-1-hexyloxy group, methanol and carbon dioxide gas Into a 500-ml autoclave (manufactured and sold by Asahi Shoko Co., Ltd., Japan) were charged 148.8 g (containing 202 mmol of Sn atoms) of the above-obtained 2-ethyl-1-hexanol solution of an organometal compound having a 2-ethyl-1-hexyloxy group and 86.4 g of 2-ethyl-1-hexanol. The autoclave was sealed and all valves were closed. Then, from a carbon dioxide gas bomb, carbon dioxide gas, the pressure of which was lowered to 3 MPa by means of a pressure regulator connected to the carbon dioxide gas bomb, was introduced into the autoclave. Stirring of the contents of the autoclave was started, and the internal temperature of the autoclave was elevated to 120° C. The internal pressure of the autoclave was adjusted to 3.5 MPa. Then, a reaction was performed for 4 hours while maintaining the internal pressure of the autoclave at 3.5 MPa, thereby obtaining a reaction mixture, and the inside of the autoclave was allowed cooled to 30° C., followed by purging of the carbon dioxide gas. The $^{119}$Sn-NMR chart of the reaction mixture is shown in FIG. 5. As shown in FIG. 5, the peak ascribed to the organometal compound of formula (1) disappeared, and several peaks were detected between −170 ppm and −230 ppm. A GC analysis of the reaction mixture showed that di(2-ethylhexyl) carbonate was obtained in a yield of 25%.

EXAMPLE 4

(Synthesis of an Organometal Compound Having a 2-ethyl-1-hexyloxy Group)

By using a 200-ml autoclave (manufactured and sold by Toyo Koatsu Co., Ltd., Japan), an organometal compound was synthesized in the same manner as in Example 1.

Step (1): Production of di(2-ethylhexyl) carbonate from an organometal compound having a 2-ethyl-1-hexyloxy group and carbon dioxide gas All valves of the above-mentioned autoclave were closed. Then, from a carbon dioxide gas bomb, carbon dioxide gas, the pressure of which was lowered to 5 MPa by means of a pressure regulator connected to the carbon dioxide gas bomb, was introduced into the autoclave. Stirring of the contents of the autoclave was started, and the internal temperature of the autoclave was elevated to 160° C. A liquid carbonic acid was gradually introduced through a feed line into the autoclave so as to adjust the internal pressure of the autoclave to 19.6 MPa. Then, a reaction was performed for 2 hours while maintaining the internal pressure of the autoclave at 19.6 MPa, thereby obtaining a reaction mixture, followed by purging of the carbon dioxide gas.

Step (2): An operation in which methanol is added to the reaction mixture to thereby effect a transesterification so as to convert the above-mentioned carbonic ester into dimethyl carbonate, and the formed dimethyl carbonate is isolated After step (1), the atmosphere in the autoclave was purged with nitrogen gas. Into the autoclave was charged 75.5 g (2.4 mol) of methanol (manufactured and sold by Aldrich, U.S.A.; a dehydrated grade), and all valves were closed. Then, stirring of the contents of the autoclave was started, and the internal temperature of the autoclave was elevated to 120° C. The stirring was continued for 2 hours and, then, methanol and dimethyl carbonate were gradually withdrawn by distillation from the autoclave through a purge line. When it was observed that there was almost no distillate any more, the inside of the autoclave was cooled, and the atmosphere in the autoclave was purged with nitrogen gas, followed by termination of the reaction. In the distillate, dimethyl carbonate was obtained in a yield of about 20%.

Step (3): Synthesis (regeneration) of an organometal compound 75 g (576 mmol) of 2-ethyl-1-hexanol (manufactured and sold by Aldrich, U.S.A.) was added to the residual liquid in the autoclave, obtained in step (2). The atmosphere in the autoclave was purged with nitrogen gas. Then, stirring of the contents of the autoclave was started, and the internal temperature of the autoclave was elevated to 192° C. The purge line was opened, and the stirring was continued for 3.5 hours under atmospheric pressure while distilling off water and 2-ethyl-1-hexanol. After that period, there was almost no distillate any more. Then, the inside of the autoclave was cooled to about 160° C. while purging the atmosphere in the autoclave with nitrogen gas, and there was obtained a reaction mixture containing an organometal compound having a 2-ethyl-1-hexyloxy group.

Step (4): Recycling of the organometal compound obtained in step (3) to step (1)

Subsequently, the same procedures as in step (1) and step (2) were successively performed as follows.

Step (1): Production of di(2-ethylhexyl) carbonate from an organometal compound having a 2-ethyl-1-hexyloxy group and carbon dioxide gas All valves of the above-mentioned autoclave were closed. Stirring of the contents of the autoclave was started. A liquid carbonic acid was gradually introduced through a feed line into the autoclave so as to adjust the internal pressure of the autoclave to 19.6 MPa. Then, a reaction was performed for 1 hour while maintaining the internal pressure of the autoclave at 19.6 MPa, thereby obtaining a reaction mixture, followed by purging of the carbon dioxide gas.

Step (2): An operation in which methanol is added to the reaction mixture to thereby effect a transesterification so as to convert the above-mentioned carbonic ester into dimethyl carbonate, and the formed dimethyl carbonate is isolated After step (1), the atmosphere in the autoclave was purged with nitrogen gas. Into the autoclave was charged 75.5 g (2.4 mol) of methanol (manufactured and sold by Aldrich, U.S.A.; a dehydrated grade), and all valves were closed. Then, stirring of the contents of the autoclave was started, and the internal temperature of the autoclave was elevated to 120° C. The stirring was continued for 1 hour and, then, methanol and dimethyl carbonate were gradually withdrawn by distillation from the autoclave through a purge line. When it was observed that there was almost no distillate any more, the inside of the autoclave was cooled, and the atmosphere in the autoclave was purged with nitrogen gas, followed by termination of the reaction. In the distillate, dimethyl carbonate was obtained in a yield of about 18%.

EXAMPLE 5

(Synthesis of an Organometal Compound Having a Hexyloxy Group, from Dibutyltin Oxide and Hexanol)

Into a 200-ml autoclave (manufactured and sold by Toyo Koatsu Co., Ltd., Japan) were charged 24.9 g (100 mmol) of dibutyltin oxide (manufactured and sold by Aldrich, U.S.A.) and 51.1 g (500 mmol) of hexanol (manufactured and sold by Aldrich, U.S.A.; a dehydrated grade), and the autoclave was sealed. The atmosphere in the autoclave was purged with nitrogen gas. Then, stirring of the contents of the autoclave was started, and the internal temperature of the autoclave was elevated to 160° C. Then, the stirring was continued for about 30 minutes. Thereafter, the valve of the purge line of the autoclave was opened, and the stirring was continued for 2 hours while blowing a small amount of nitrogen gas into the bottom of the autoclave and distilling off water and hexanol through the purge line. After that period, there was almost no distillate any more. Then, the inside of the autoclave was cooled to about 30° C., and there was obtained a reaction mixture. A $^{119}$Sn-NMR analysis of the reaction mixture was performed. The $^{119}$Sn-NMR analysis showed that there were obtained about 47 mmol of 1,1,3,3-tetrabutyl-1,3-di-hexyloxy-di-stannoxane and about 6 mmol of dibutyltin dihexyloxide.

Step (1): Production of dihexyl carbonate from an organometal compound having a hexyloxy group, hexanol and carbon dioxide gas Into the above-mentioned 200-ml autoclave containing the reaction mixture (containing an organometal compound having a hexyloxy group) was charged 61.5 g (602 mmol) of hexanol (manufactured and sold by Aldrich, U.S.A.; a dehydrated grade), and the autoclave was sealed. Then, from a carbon dioxide gas bomb, carbon dioxide gas, the pressure of which was lowered to 5 MPa by means of a pressure regulator connected to the carbon dioxide gas bomb, was introduced into the autoclave. Stirring of the contents of the autoclave was started. 10 Minutes after the start of the stirring, the valve of the carbon dioxide gas bomb was closed. Then, the internal temperature of the autoclave was elevated to 180° C. while stirring. In this instant, the internal pressure of the autoclave was about 7.5 MPa. Then, a reaction was performed for 6 hours while maintaining the internal pressure of the autoclave at about 7.5 MPa. Thereafter, the inside of the autoclave was cooled to about 30° C. and the internal pressure of the autoclave was returned to atmospheric pressure by gently purging the carbon dioxide gas, and there was obtained a transparent reaction mixture. In the reaction mixture, dihexyl carbonate was obtained in a yield of about 14%.

Step (2): An operation in which hexanol containing 1% by weight of water is added to the reaction mixture obtained in step (1) to thereby form solids, and the solids are removed by filtration, whereupon the resultant filtrate is subjected to distillation, so that dihexyl carbonate is obtained as a distillate After step (1), 10 g of hexanol containing 1% by weight of water was gently added to the reaction mixture obtained in step (1), and the resultant mixture was stirred for about 30 minutes. Then, the autoclave was opened, and it was found that the mixture in the autoclave had turned into a white slurry. The white slurry was subjected to filtration using a membrane filter (H020A142C, manufactured and sold by Advantec Toyo Kaisha, Ltd., Japan) to thereby obtain white solids and a filtrate. The white solids were washed 2 times with 20 ml of hexanol. The filtrate was transferred into a 1-liter eggplant-shaped flask and subjected to distillation under heating in an oil bath at 150° C. and under a pressure of 1 KPa. By the distillation, hexanol and dihexyl carbonate were recovered. The yield of dihexyl carbonate was 13%.

Step (3): Synthesis (regeneration) of an organometal compound

The white solids obtained in step (2) and a residual viscous liquid which remained in the flask after the distillation performed in step (2), were charged into a 200-ml autoclave (manufactured and sold by Toyo Koatsu Co., Ltd., Japan). Further, 51.1 g (500 mmol) of hexanol (manufactured and sold by Aldrich, U.S.A.; a dehydrated grade) was charged into the autoclave, and the autoclave was sealed. The atmosphere in the autoclave was purged with nitrogen gas. Then, stirring of the contents of the autoclave was started, and the internal temperature of the autoclave was elevated to 160° C. Then, the stirring was continued for about 30 minutes. Thereafter, the purge line of the autoclave was opened, and the stirring was continued for 2 hours while blowing a small amount of nitrogen gas into the bottom of the autoclave and distilling off water and hexanol through the purge line. After that period, there was almost no distillate any more. Then, the inside of the autoclave was cooled to about 30° C., and there was obtained a reaction mixture. A $^{119}$Sn-NMR analysis of the reaction mixture was performed. The $^{119}$Sn-NMR analysis showed that there were obtained about 47 mmol of 1,1,3,3-tetrabutyl-1,3-di-hexyloxy-di-stannoxane and about 6 mmol of dibutyltin dihexyloxide.

Step (4): Recycling of the organometal compound obtained in step (3) to step (1)

Subsequently, the same procedures as in step (1) and step (2) were successively performed as follows.

Step (1): Production of dihexyl carbonate from the organometal compound obtained in step (3)

Into the above-mentioned autoclave in which step (3) was performed was charged 61.5 g (602 mmol) of hexanol (manufactured and sold by Aldrich, U.S.A.; a dehydrated grade), and the autoclave was sealed. Then, from a carbon dioxide gas bomb, carbon dioxide gas, the pressure of which was lowered to 5 MPa by means of a pressure regulator connected to the carbon dioxide gas bomb, was introduced into the autoclave. Stirring of the contents of the autoclave was started. 10 Minutes after the start of the stirring, the valve of the carbon dioxide gas bomb was closed. Then, the internal temperature of the autoclave was elevated to 180° C. while stirring. In this instant, the internal pressure of the autoclave was about 7.5 MPa. Then, a reaction was performed for 6 hours while maintaining the internal pressure of the autoclave at about 7.5 MPa. Thereafter, the inside of the autoclave was cooled to about 30° C. and the internal pressure of the autoclave was returned to atmospheric pressure by gently purging the carbon dioxide gas through the purge line, and there was obtained a transparent reaction mixture. In the reaction mixture, dihexyl carbonate was obtained in a yield of about 14%.

Step (2): An operation in which hexanol containing 1% by weight of water is added to the reaction mixture obtained in step (1) to thereby form solids, and the solids are removed by filtration, whereupon the resultant filtrate is subjected to distillation, so that dihexyl carbonate is obtained as a distillate After step (1), 10 g of hexanol containing 1% by weight of water was gently added to the reaction mixture obtained in step (1), and the resultant mixture was stirred for about 30 minutes. Then, the autoclave was opened, and it was found that the mixture in the autoclave had turned into a white slurry. The white slurry was subjected to filtration using a membrane filter (H020A142C, manufactured and sold by Advantec Toyo Kaisha, Ltd., Japan) to thereby obtain white solid and a filtrate. The white solids were washed 2 times with 20 ml of hexanol. The filtrate was transferred into a 1-liter eggplant-shaped flask and subjected to distillation under heating. By the distillation, hexanol and dihexyl carbonate were recovered. The yield of dihexyl carbonate was 13%.

EXAMPLE 6

Production of Dihexyl Carbonate (Synthesis of Dibutyltin Dihexyloxide)

Into a 200-ml eggplant-shaped flask equipped with a condenser and a Dean-Stark trap were charged 12.5 g (50 mmol) of dibutyltin oxide (manufactured and sold by Aldrich, U.S.A.), 50 ml of hexanol (manufactured and sold by Aldrich, U.S.A.; a dehydrated grade), 100 ml of xylene and a stirrer. Then, the eggplant-shaped flask was heated using an oil bath while stirring the contents of the eggplant-shaped flask, and the temperature of the eggplant-shaped flask was elevated to a temperature at which reflux of the xylene occurred. The reflux of the xylene was performed under heating for about 4 hours while distilling off water, so that about 0.8 ml of water was collected in the Dean-Stark trap. The Dean-Stark trap was detached from the eggplant-shaped flask, and xylene and hexanol were removed from the eggplant-shaped flask by an ordinary distillation. Further, an excess amount of hexanol was removed from the eggplant-shaped flask by reduced pressure distillation, thereby obtaining a viscous, transparent liquid. Then, the atmosphere in the eggplant-shaped flask was purged with nitrogen, and the inside of the eggplant-shaped flask was cooled. The resultant reaction mixture was subjected to a $^{119}$Sn-NMR analysis. In the $^{119}$Sn-NMR chart of the reaction mixture, a peak ascribed to dibutyltin dihexyloxide was detected at −134 ppm, and peaks ascribed to a small amount of 1,1,3,3-tetrabutyl-1,3-dihexyloxydistannoxane were, respectively, detected at −177 ppm and −187 ppm.

Step (1): Production of dihexyl carbonate from dibutyltin dihexyloxide

Into a 100-ml autoclave (manufactured and sold by Toyo Koatsu Co., Ltd., Japan) were charged about 2.2 g of an organometal compound containing about 5 mmol of dibutyltin dihexyloxide (wherein the organometal compound was contained in the above-obtained reaction mixture) and 25.5 g (250 mmol) of hexanol (manufactured and sold by Aldrich, U.S.A.; a dehydrated grade). The autoclave was sealed. Then, from a carbon dioxide gas bomb, carbon dioxide gas, the pressure of which was lowered to 4 MPa by means of a pressure regulator connected to the carbon dioxide gas bomb, was introduced into the autoclave. Stirring of the contents of the autoclave was started. 10 Minutes after the start of the stirring, the valve of the carbon dioxide gas bomb was closed. Then, the internal temperature of the autoclave was elevated to 120° C. while stirring. Thereafter, carbon dioxide gas was gradually withdrawn from the autoclave through a purge line so as to adjust the internal pressure of the autoclave to 4 MPa. Then, a reaction was performed for 100 hours while maintaining the internal pressure of the autoclave at 4 MPa. After that period, the inside of the autoclave was cooled to about 30° C., and the internal pressure of the autoclave was returned to atmospheric pressure by gently purging the carbon dioxide gas through a purge line, and there was obtained a transparent reaction mixture. In the reaction mixture, dihexyl carbonate was obtained in a yield of 18%.

Step (2): An operation in which hexanol containing 1% by weight of water is added to the reaction mixture obtained in step (1) to thereby form solids, and the solids are removed by filtration, whereupon the resultant filtrate is subjected to distillation, so that dihexyl carbonate is obtained as a distillate After step (1), 10 g of hexanol containing 1% by weight of water was gently added to the reaction mixture obtained in step (1), and the resultant mixture was stirred for about 30 minutes. Then, the autoclave was opened, and it was found that the mixture in the autoclave had turned into a white slurry. The white slurry was subjected to filtration using a membrane filter (H020A142C, manufactured and sold by Advantec Toyo Kaisha, Ltd., Japan) to thereby obtain white solids and a filtrate. The white solids were washed 2 times with 20 ml of hexanol. The filtrate was transferred into a 1-liter eggplant-shaped flask and subjected to distillation under heating. By the distillation, hexanol and dihexyl carbonate were recovered. The yield of dihexyl carbonate was 17%.

Step (3): Synthesis (regeneration) of an organometal compound

The white solids obtained in step (2) and a residual viscous liquid which remained in the flask after the distillation performed in step (2), were charged into a 100-ml eggplant-shaped flask equipped with a condenser and a Dean-Stark trap. Further, 20 ml of hexanol (manufactured and sold by Aldrich, U.S.A.; a dehydrated grade), 30 ml of xylene and a stirrer were charged into the eggplant-shaped flask. Then, the eggplant-shaped flask was heated using an oil bath while stirring the contents of the eggplant-shaped flask, and the temperature of the eggplant-shaped flask was elevated to a temperature at which reflux of the xylene occurred. The reflux of the xylene was performed under heating for about 4 hours while distilling off water, so that about 0.1 ml of water was collected in the Dean-Stark trap. The Dean-Stark trap was detached from the eggplant-shaped flask, and xylene and hexanol were removed from the eggplant-shaped flask by an ordinary distillation. Further, an excess amount of hexanol was removed from the eggplant-shaped flask by reduced pressure distillation, thereby obtaining a viscous, transparent liquid. Then, the atmosphere in the eggplant-shaped flask was purged with nitrogen, and the inside of the eggplant-shaped flask was cooled. The resultant reaction mixture was subjected to a $^{119}$Sn-NMR analysis. In the $^{119}$Sn-NMR chart of the reaction mixture, a peak ascribed to dibutyltin dihexyloxide was detected at −134 ppm, and peaks ascribed to a small amount of 1,1,3,3-tetrabutyl-1,3-dihexyloxydistannoxane were, respectively, detected at −177 ppm and −187 ppm.

Step (4): Recycling of the organometal compound obtained in step (3) to step (1)

Subsequently, the same procedures as in step (1) and step (2) were successively performed as follows.

Step (1): Production of dihexyl carbonate from the organometal compound obtained in step (3)

Into a 100-ml autoclave (manufactured and sold by Toyo Koatsu Co., Ltd., Japan) were charged about 2.2 g of an organometal compound containing about 5 mmol of dibutyltin dihexyloxide (wherein the organometal compound was contained in the above-obtained reaction mixture) and 25.5 g (250 mmol) of hexanol (manufactured and sold by Aldrich, U.S.A.; a dehydrated grade). The autoclave was sealed. Then, from a carbon dioxide gas bomb, carbon dioxide gas, the pressure of which was lowered to 4 MPa by means of a pressure regulator connected to the carbon dioxide gas bomb, was introduced into the autoclave. Stirring of the contents of the autoclave was started. 10 Minutes after the start of the stirring, the valve of the carbon dioxide gas bomb was closed. Then, the internal temperature of the autoclave was elevated to 120° C. while stirring. Thereafter, carbon dioxide gas was gradually withdrawn from the autoclave through a purge line so as to adjust the internal pressure of the autoclave to 4 MPa. Then, a reaction was performed for 100 hours while maintaining the internal pressure of the autoclave at 4 MPa. After that period, the inside of the autoclave was cooled to about 30° C., and the internal pressure of the autoclave was returned to atmospheric pressure by gently purging the carbon dioxide gas through a purge line, and there was obtained a transparent reaction mixture. In the reaction mixture, dihexyl carbonate was obtained in a yield of 17%.

Step (2): An operation in which hexanol containing 1% by weight of water is added to the reaction mixture obtained in step (1) to thereby form solids, and the solids are removed by filtration, whereupon the resultant filtrate is subjected to distillation, so that dihexyl carbonate is obtained as a distillate After step (1), 10 g of hexanol containing 1% by weight of water was gently added to the reaction mixture obtained in step (1), and the resultant mixture was stirred for about 30 minutes. Then, the autoclave was opened, and it was found that the mixture in the autoclave had turned into a white slurry. The white slurry was subjected to filtration using a membrane filter (H020A142C, manufactured and sold by Advantec Toyo Kaisha, Ltd., Japan) to thereby obtain white solids and a filtrate. The white solids were washed 2 times with 20 ml of hexanol. The filtrate was transferred into a 1-liter eggplant-shaped flask and subjected to distillation under heating. By the distillation, hexanol and dihexyl carbonate were recovered. The yield of dihexyl carbonate was 16%.

EXAMPLE 7

(Synthesis of Dimethyl Carbonate)
Step (1): Production of dimethyl carbonate from dibutyltin dimethoxide and methanol Into a 10-ml high-pressure reactor (manufactured and sold by Thar Designs Inc., U.S.A.) equipped with a valve were charged 1.48 g (5 mmol) of dibuthyltin dimethoxide (manufactured and sold by Aldrich, U.S.A.), 1.6 g (50 mmol) of methanol (manufactured and sold by Wako Pure Chemical Industries Ltd., Japan; a dehydrated grade) and a SUS ball (which was for use in stirring the contents of the reactor). The inside of the reactor was cooled to about −68° C. with a dry ice/ethanol mixture. Then, from a carbon dioxide gas bomb, 2.0 g of a high purity carbon dioxide gas, the pressure of which was lowered to about 2 MPa by means of a pressure regulator connected to the carbon dioxide gas bomb, was gently introduced into the high pressure reactor. Thereafter, the reactor was placed in an oil bath which was maintained at 150° C., and shaken for 15 hours. After that period, the inside of the reactor was cooled to about 20° C., and the internal pressure of the reactor was returned to atmospheric pressure by gently purging an excess amount of the carbon dioxide gas, thereby obtaining a reaction mixture. In the reaction mixture, dimethyl carbonate was obtained in a yield of 30%.

Step (2): An operation in which methanol containing water is added to the reaction mixture obtained in step (1) to thereby obtain a mixture having solids deposited therein, and the mixture containing solids is subjected to distillation To the reaction mixture (contained in the reactor) obtained in step (1) was added 2 ml of methanol containing 10% by weight of water, and the reactor was shaken at room temperature (about 20° C.) for about 5 minutes. Then, the reactor was opened, and it was found that the mixture in the reactor had turned into a white slurry. The obtained white slurry was transferred to a 50-ml eggplant-shaped flask, and subjected to distillation under heating. By the distillation, methanol and dimethyl carbonate were recovered. The yield of dimethyl carbonate was 29%.

EXAMPLE 8

(Production a Metal Methoxide from Dibutyltin Oxide and Methanol by Azeotropic Distillation of Water)

2.5 g of dibutyltin oxide (manufactured and sold by Aldrich, U.S.A.), 32.0 g of methanol (manufactured and sold by Wako Pure Chemical Industries Ltd., Japan; a reagent grade) and 100 ml of hexane (manufactured and sold by Wako Pure Chemical Industries Ltd., Japan; a reagent grade) were charged into a 200-ml three-necked flask equipped with a liquid transferring pump and a Liebig condenser connected to a trap. The three-necked flask was placed in an oil bath which was maintained at 80° C., and distillation was performed under heating for 4 hours while stirring the contents of the flask using a stirrer. During the distillation, the amounts of hexane and methanol removed from the three-necked flask were measured, and fresh hexane and methanol were charged into the three-necked flask by means of the liquid transferring pump, in amounts which were, respectively, the same as the amounts of hexane and methanol removed from the three-necked flask, so as to keep constant the amounts of the hexane and methanol in the three-necked flask. After the distillation, the inside of the three-necked flask was cooled to 30° C., and hexane and an excess amount of methanol were removed from the flask by reduced pressure distillation, thereby obtaining a viscous, transparent liquid. The obtained liquid was subjected to a $^{119}$Sn-NMR analysis. In the $^{119}$Sn-NMR chart of the obtained liquid, peaks were, respectively, detected at −174 ppm and −180 ppm.

Step (1): An operation in which methanol is added to the above-obtained liquid, and a reaction is performed in the presence of a high pressure carbon dioxide gas Into a 10-ml high pressure reactor (manufactured and sold by Thar Designs Inc., U.S.A.) equipped with a valve were charged 0.66 g of the above-obtained liquid (containing an organometal compound), 1.6 g of methanol and a SUS316 ball (which was for use in stirring the contents in the reactor). The inside of the reactor was cooled to about −68° C. with a dry ice/ethanol mixture. Then, from a carbon dioxide gas bomb, 2.8 g of a high purity carbon dioxide gas, the pressure of which was lowered to about 2 MPa by means of a pressure regulator connected to the carbon dioxide gas bomb, was gently introduced into the high pressure reactor. Thereafter, the reactor was placed in an oil bath which was maintained at 160° C., and shaken for 15 hours. After that period, the inside of the reactor was cooled to about 20° C., and the internal pressure of the reactor was returned to atmospheric pressure by gently purging an excess amount of the carbon dioxide gas, thereby obtaining a white slurry as a reaction mixture. In the reaction mixture, dimethyl carbonate was obtained in a yield of 6%.

Step (2): Isolation of dimethyl carbonate

To the white slurry (contained in the high pressure reactor) obtained in step (1) was added 10 ml of methanol. Then, the resultant in the high pressure reactor was transferred to a 50-ml eggplant-shaped flask. The contents of the eggplant-shaped flask were subjected to distillation under heating using an oil bath which was maintained at 90° C. By the distillation, methanol and dimethyl carbonate were recovered, leaving a residual liquid in the flask. The yield of dimethyl carbonate was 6%.

Step (3): Synthesis (regeneration) of an organometal compound

The residual liquid which remained in the flask after the recovery of dimethyl carbonate by distillation performed in step (2) was transferred to a 100-ml three-necked flask equipped with a liquid transferring pump and a Liebig condenser connected to a trap. Into the three-necked flask were charged a stirrer, 30 ml of hexane and 30 ml of methanol. The three-necked flask was placed in an oil bath which was maintained at 80° C., and distillation was performed under heating for 4 hours while stirring the contents of the flask using the stirrer. During the distillation, the amounts of hexane and methanol removed from the three-necked flask were measured, and fresh hexane and methanol were charged into the three-necked flask by means of the liquid transferring pump, in amounts which were, respectively, the same as the amounts of hexane and methanol removed from three-necked flask, so as to keep constant the amounts of hexane and methanol in the three-necked flask. After the distillation, the inside of the three-necked flask was cooled to 30° C., and hexane and an excess amount of methanol were removed from the flask by reduced pressure distillation, thereby obtaining a viscous, transparent liquid. The obtained liquid was subjected to a $^{119}$Sn-NMR analysis. In the $^{119}$Sn-NMR chart of the obtained liquid, peaks were, respectively, detected at −174 ppm and −180 ppm.

EXAMPLE 9

Step (1): Production of a carbonic ester from dibutyltin dibutoxide and an alcohol Into a 10-ml high pressure reactor (manufactured and sold by Thar Designs Inc., U.S.A) equipped with a valve were charged 1.48 g (4 mmol) of dibutyltin dibutoxide (manufactured and sold by Aldrich, U.S.A.), 2.22 g (30 mmol) of butanol (manufactured and sold by Wako Pure Chemical Industries Ltd., Japan; a dehydrated grade), 1.38 g (30 mmol) of ethanol (manufactured and sold by Wako Pure Chemical Industries Ltd., Japan; a dehydrated grade) and a SUS ball (which was for use in stirring the contents of the reactor). The inside of the reactor was cooled to about −68° C. with a dry ice/ethanol mixture. Then, from a carbon dioxide gas bomb, 2.0 g of a high purity carbon dioxide gas, the pressure of which was lowered to about 2 MPa by means of a pressure regulator connected to the carbon dioxide gas bomb, was gently introduced into the high pressure reactor. Thereafter, the reactor was placed in an oil bath which was maintained at 150° C., and shaken for 22 hours. After that period, the inside of the reactor was cooled to about 20° C., and the internal pressure of the reactor was returned to atmospheric pressure by gently purging an excess amount of the carbon dioxide gas, thereby obtaining a transparent reaction mixture. In the reaction mixture, ethylbutyl carbonate, dibutyl carbonate and diethyl carbonate were obtained in yields of 25%, 10% and 6%, respectively.

Step (2): Recovering of carbonic esters by distillation from the reaction mixture obtained in step (1)

The reaction mixture obtained in step (1) was transferred to a 50-ml eggplant-shaped flask, and subjected to distillation under reduced pressure. By the distillation, ethanol, butanol and carbonic esters were recovered. With respect to the yields of the recovered carbonic esters, ethylbutyl carbonate, dibutyl carbonate and diethyl carbonate were obtained in yields of 23%, 8% and 5%, respectively.

EXAMPLE 10

Step (1): An operation in which methanol is added to a viscous, transparent liquid (containing an organometal compound) which is obtained in substantially the same manner as in Example 8, and a reaction is performed in the presence of a high pressure carbon dioxide gas Into a SUS316 tube reactor (volume: 8 ml; outer diameter: 12.7 mm; wall thickness: 2.1 mm) equipped with a SUS316 conduit and a valve were charged 1.1 g of a viscous, transparent liquid (containing an organometal compound) which was obtained in substantially the same manner as in Example 8, 2.6 g of methanol and a SUS316 ball (which was for use in stirring the contents of the reactor). The inside of the reactor was cooled to about −68° C. with a dry ice/ethanol mixture. Then, from a carbon dioxide gas bomb, 2.8 g of a high purity carbon dioxide gas, the pressure of which was lowered to about 2 MPa by means of a pressure regulator connected to the carbon dioxide gas bomb, was gently introduced into the tube reactor. Thereafter, the reactor was placed in an oil bath which was maintained at 150° C., and shaken for 12 hours. After that period, the inside of the reactor was cooled to 20° C., and the internal pressure of the reactor was returned to atmospheric pressure by gently purging an excess amount of the carbon dioxide gas, thereby obtaining a white slurry as a reaction mixture. In the reaction mixture, dimethyl carbonate was obtained in a yield of about 5%.

EXAMPLE 11

(Production of an Organometal Compound Having a Hexyloxy Group from Dibutyltin Oxide and n-hexanol)

Into a 300-ml eggplant-shaped flask equipped with a condenser and a Dean-Stark trap were charged 24.9 g of dibutyltin oxide (manufactured and sold by Aldrich, U.S.A.), 40.9 g of n-hexanol (manufactured and sold by Wako Pure Chemical Industries, Ltd., Japan; a reagent grade) and 150 ml of toluene (manufactured and sold by Wako Pure Chemical Industries, Ltd., Japan; a reagent grade). The flask was placed in an oil bath which was maintained at 120° C., and the contents of the flask were refluxed under heating for 12 hours while stirring. After that period, the inside of the flask was cooled to 80° C., and an excess amount of n-hexanol was removed from the reactor by reduced pressure distillation, thereby obtaining a liquid containing 75.1 g of an organometal compound. Subsequently, the obtained liquid was subjected to a $^{119}$Sn-NMR analysis. In the $^{119}$Sn-NMR chart of the liquid, a peak ascribed to the organometal compound of formula (1) was detected at −130 ppm, and peaks ascribed to the organometal compound of formula (2) were, respectively, detected at −177 ppm and −186 ppm.

Step (1): Production of dihexyl carbonate from an organometal compound and hexanol while introducing carbon dioxide gas having an atmospheric pressure Into a two-necked flask equipped with a condenser was inserted an injection tube which had connected thereto a glass ball filter (G2) (manufactured and sold by Vidrex Co., Ltd., Japan). Further, a stirrer was placed in the flask. Into the two-necked flask were charged 0.75 g of the above-obtained liquid (containing an organometal compound) and 41 g of n-hexanol. Then, introduction of a high purity carbon dioxide gas into the flask through the injection tube was started at a flow rate of 100 ml/min. The flask was heated using an oil bath (which was maintained at 130° C.) while stirring the contents of the flask and introducing a high purity carbon dioxide gas into the flask, thereby producing dihexyl carbonate. 288 hours after the start of the heating of the flask, the yield of dihexyl carbonate was 40%.

EXAMPLE 12

(Production of a Metal Cyclohexyloxide from Dibutyltin Oxide and Cyclohexanol by Azeotropic Distillation of Water)

Into a 500-ml eggplant-shaped flask equipped with a condenser and a Dean-Stark trap were charged 5.1 g of dibutyltin oxide (manufactured and sold by Aldrich, U.S.A.), 80.1 g of cyclohexanol (manufactured and sold by Wako Pure Chemical Industries, Ltd., Japan; a reagent grade) and 300 ml of toluene (manufactured and sold by Wako Pure Chemical Industries, Ltd., Japan; a reagent grade). The flask was placed in an oil bath which was maintained at 130° C., and the contents of the flask were refluxed under heating for 12 hours while stirring. After that period, the inside of the flask was cooled to 80° C. An excess amount of cyclohexanol was removed from the flask by reduced pressure distillation, thereby obtaining a liquid containing 15.2 g of an organometal compound. Subsequently, the obtained liquid was subjected to a $^{119}$Sn-NMR analysis. In the $^{119}$Sn-NMR chart of the liquid, peaks ascribed to the organometal compound of formula (2) were, respectively, detected at −176 ppm and −190 ppm.

Step (1): Production of dicyclohexyl carbonate, in which cyclohexanol is added to the above-obtained liquid, and a reaction is performed in the presence of a high pressure carbon dioxide gas Into a SUS316 tube reactor (volume: 8 ml; outer diameter: 12.7 mm; wall thickness: 2.1 mm) equipped with a SUS316 conduit and a valve were charged 0.86 g of the above-obtained liquid containing an organometal compound, 1.0 g of cyclohexanol and a SUS316 ball (which was for use in stirring the contents of the reactor). The inside of the reactor was cooled to about −68° C. with a dry ice/ethanol mixture. Then, from a carbon dioxide gas bomb, 2.0 g of a high purity carbon dioxide gas, the pressure of which was lowered to about 2 MPa by means of a pressure regulator connected to the carbon dioxide gas bomb, was gently introduced into the reactor. The reactor was placed in an oil bath which was maintained at 130° C., and shaken for 14 hours. After that period, the inside of the reactor was cooled to 20° C., and the internal pressure of the reactor was returned to atmospheric pressure by gently purging an excess amount of the carbon dioxide gas, thereby obtaining a transparent reaction mixture. The obtained transparent reaction mixture was analyzed. As a result, it was found that dicyclohexyl carbonate was obtained in a yield of 40%.

EXAMPLE 13

Production of Methylethyl Carbonate

Step (1): Production of methylethyl carbonate from titanium tetramethoxide, carbon dioxide gas, methanol and ethanol Into a 10-ml high pressure reactor (manufactured and sold by Thar Designs Inc., U.S.A.) equipped with a valve were charged 0.9 g (5 mmol) of titanium tetramethoxide (manufactured and sold by AZmax. co., Japan), about 0.9 g (30 mmol) of methanol (manufactured and sold by Wako Pure Chemical Industries, Ltd., Japan; a dehydrated grade), about 1.4 g (30 mmol) of ethanol (manufactured and sold by Wako Pure Chemical Industries, Ltd., Japan; a dehydrated grade) and a SUS ball (which was for use in stirring the contents of the reactor).

The inside of the reactor was cooled to about −68° C. with a dry ice/ethanol mixture. Then, from a carbon dioxide gas bomb, 2.0 g of a high purity carbon dioxide gas, the pressure of which was lowered to about 2 MPa by means of a pressure regulator connected to the carbon dioxide gas bomb, was gently introduced into the autoclave. The reactor was placed in an oil bath which was maintained at 150° C., and shaken for 15 hours. After that period, the inside of the reactor was cooled to about 20° C., and the internal pressure of the reactor was returned to atmospheric pressure by gently purging an excess amount of the carbon dioxide gas, thereby obtaining a white slurry as a reaction mixture. In the reaction mixture, methylethyl carbonate, dimethyl carbonate and diethyl carbonate were obtained in yields of 25%, 3% and 4%, respectively.

Step (2): Isolation of carbonic esters

The above-obtained slurry was transferred into a 50-ml eggplant-shaped flask, and subjected to a reduced pressure distillation at 30° C. By the distillation, carbonic esters were recovered. With respect to the yields of the recovered carbonic esters, methylethyl carbonate, dimethyl carbonate and diethyl carbonate were obtained in yields of 23%, 2% and 3%, respectively.

COMPARATIVE EXAMPLE

In this Comparative Example, production of dimethyl carbonate from dibutyltin oxide (which does not have a metal-oxygen-carbon linkage), methanol and carbon dioxide gas was attempted as described below.

There was provided a 200-ml autoclave (manufactured and sold by Toyo Koatsu Co., Ltd., Japan) which had connected thereto a line for introducing a liquid carbonic acid and carbon dioxide gas, a distillate withdrawal line, a sampling tube and a line for introducing nitrogen gas into the bottom of the autoclave. Into the 200-ml autoclave were charged 15.0 g (60 mmol) of dibutyltin oxide (manufactured and sold by Aldrich, U.S.A.) and 48.1 g (1.5 mol) of methanol. All valves were closed. Then, from a carbon dioxide gas bomb, carbon dioxide gas, the pressure of which was lowered to 5 MPa by means of a pressure regulator connected to the carbon dioxide gas bomb, was introduced into the autoclave. Stirring of the contents of the autoclave was started, and the internal temperature of the autoclave was elevated to 160° C. A liquid carbonic acid was gradually introduced through a feed line into the autoclave so as to adjust the internal pressure of the autoclave to 22 MPa. Then, a reaction was performed for 16 hours while maintaining the internal pressure of the autoclave at 22 MPa. After that period, the inside of the autoclave was cooled to about 30° C., followed by purging of the carbon dioxide gas, thereby obtaining a white slurry as a reaction mixture. The obtained reaction mixture was analyzed by gas chromatography (GC). In the analysis by GC, no dimethyl carbonate was detected in the reaction mixture.

INDUSTRIAL APPLICABILITY

By the method of the present invention, a carbonic ester can be produced in high yield from an organometal compound having a metal-oxygen-carbon linkage and carbon dioxide. It is advantageous that carbon dioxide has no toxicity and no corrosiveness and is inexpensive. Further, the method of the present invention is advantageous not only in that the organometal compound after use in this method can be regenerated and recycled to step (1) of the method, thereby preventing occurrence of wastes derived from the organometal compound, but also in that there is no need for the use of a large amount of a dehydrating agent, thereby preventing occurrence of wastes derived from the dehydrating agent.

Therefore, the method of the present invention is commercially very useful and has high commercial value.

The invention claimed is:

1. A method for producing a symmetrical carbonic ester, comprising:
   (1) performing a reaction between an organometal compound having a metal-oxygen-carbon linkage and carbon dioxide to obtain a reaction mixture containing a carbonic ester formed by the reaction,
   (2) separating said carbonic ester from said reaction mixture to obtain a residual liquid, and
   (3) reacting said residual liquid with a first alcohol to form at least one organometal compound having a metal-oxygen-carbon linkage and form water and removing said water from said at least one organometal compound, wherein said at least one organometal compound obtained in step (3) is recovered for recycle thereof to step (1),
   wherein said organometal compound used in step (1) comprises at least one compound selected from the group consisting of:
   an organometal compound represented by the formula (1):

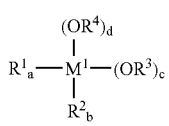

wherein:
   $M^1$ represents a tin atom;
   each of $R^1$ and $R^2$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;
   each of $R^3$ and $R^4$ represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and
   each of a and b is an integer of from 0 to 2, a+b=0 to 2 each of c and d is an integer of from 0 to 4, and a+b+c+d=4; and
   an organometal compound represented by the formula (2):

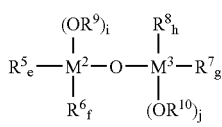

wherein:
   each of $M^2$ and $M^3$ represents a tin atom;
   each of $R^5$, $R^6$, $R^7$ and $R^8$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;
   each of $R^9$ and $R^{10}$ represents a straight chain branched $C_1$-$C_{12}$ alkyl group, a $C_5$-$C_{12}$ cyloalkyl group, a straight chain or branched $C_2$-$C_{12}$ alkenyl group, or a $C_7$-$C_{20}$ araklyl group comprised of unsubstituted or substituted $C_6$-$C_{19}$ aryl and alkyl selected from the group consisting of straight chain or branched $C_1$-$C_{14}$ and $C_5$-$C_{14}$ cycloalkyl; and
   e+f=0 to 2, g+h=0 to 2, each of i and j is independently an integer of from 1 to 3, e+f+i=3 and g+h+j=3,
   wherein $R^3$ and $R^4$ in formula (1) and $R^9$ and $R^{10}$ in formula (2) are the same, and
   wherein said first alcohol used in step (3) has an organic group which is the same as the alkoxy group of the organometal compound used in step (1).

2. The method according to claim 1, wherein, in step (1), said organometal compound is used in an amount which is 1/50 to 1 time the stoichiometric amount relative to the amount of said carbon dioxide.

3. The method according to claim 2, wherein said reaction in step (1) is performed at 20° C. or more.

4. The method according to claim 1, wherein said reaction in step (1) is performed in the presence of a second alcohol which is the same as said first alcohol used in step (3),
   said second alcohol used in step (1) having an organic group which is the same as the alkoxy group of organometal compound used in step (1).

5. The method according to claim 1, wherein said separation of said carbonic ester in step (2) is performed in the presence of a third alcohol which is the same as said first alcohol used in step (3),
   said third alcohol used in step (2) having an organic group which is the same as the alkoxy group of the organometal compound used in step (1).

6. The method according to claim 1, wherein said separation of said carbonic ester in step (2) is performed by at least one separation method selected from the group consisting of distillation, extraction and filtration.

7. The method according to claim 1, wherein said removal of said water in step (3) is performed by membrane separation.

8. The method according to claim 7, wherein said membrane separation is pervaporation.

9. The method according to claim 1, wherein said removal of said water in step (3) is performed by distillation.

10. The method according to claim 1, wherein said first alcohol used in step (3) is at least one alcohol selected from the group consisting of an alkyl alcohol having a straight chain or branched $C_1$-$C_{12}$ alkyl group, a cycloalkyl alcohol having a $C_5$-$C_{12}$ cycloalkyl group, an alkenyl alcohol having a straight chain or branched $C_2$-$C_{12}$ alkenyl group, and an aralkyl alcohol having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl.

11. The method according to claim 10, wherein each of said alkyl alcohol, said cycloalkyl alcohol, said alkenyl alcohol and said aralkyl alcohol has a boiling point which is higher than the boiling point of water.

12. The method according to claim 11, wherein said alkyl alcohol comprises at least one member selected from the group consisting of n-butyl alcohol, isobutyl alcohol and an alkyl alcohol having a straight chain or branched $C_5$-$C_{12}$ alkyl group, and said alkenyl alcohol has a straight chain or branched $C_4$-$C_{12}$ alkenyl group.

13. The method according to claim 1, wherein each of $R^3$ and $R^4$ in formula (1) and $R^9$ and $R^{10}$ in formula (2) represents an n-butyl group, an isobutyl group, a straight chain or branched $C_5$-$C_{12}$ alkyl group, or a straight chain or branched $C_4$-$C_{12}$ alkenyl group.

14. The method according to claim 1 or 13, wherein, in step (1), said organometal compound is used in at least one form selected from the group consisting of a monomeric form, an oligomeric form, a polymeric form and an associated form.

15. The method according to any one of claims 1 to 3, 4 to 13, which further comprises, after step (3), a step (4) in which said at least one organometal compound recovered in step (3) is recycled to step (1), followed by repeating of a sequence of steps (1) to (4) one or more times.

16. The method according to claim 15, wherein said organometal compound used in step (1) is produced from an organotin oxide and an alcohol.

17. The method according to claim 1, wherein said organometal compound represented by formula (1) is a diakyltin dialkoxide, and said organometal compound represented by formula (2) is a tetraalkyldialkoxydistannoxane, and
    wherein each of $R^1$ and $R^2$ in formula (1) and $R^5$, $R^6$, $R^7$, and $R^8$ in formula (2) independently represents a straight chain or branched $C_1$-$C_{12}$ alkyl group.

18. The method according to claim 17, wherein said dialkyltin dialkoxide is a dibutyltin dialkoxide, and said tetraalkyldialkoxydistannoxane is a tetrabutyldialkoxydistannoxane.

* * * * *